US008642505B2

(12) United States Patent
Kohn

(10) Patent No.: US 8,642,505 B2
(45) Date of Patent: *Feb. 4, 2014

(54) CONTROL OF SHOOT/FOLIAR FEEDING PESTS WITH PESTICIDE SEED TREATMENTS

(75) Inventor: Frank C. Kohn, St. Louis, MO (US)

(73) Assignee: Monsanto Technology, LLC, St. Louis, MO (US)

( * ) Notice: Subject to any disclaimer, the term of this patent is extended or adjusted under 35 U.S.C. 154(b) by 737 days.

This patent is subject to a terminal disclaimer.

(21) Appl. No.: 11/998,776

(22) Filed: Nov. 30, 2007

(65) Prior Publication Data

US 2008/0092256 A1 Apr. 17, 2008

Related U.S. Application Data

(63) Continuation of application No. 10/658,923, filed on Sep. 9, 2003, now abandoned, which is a continuation of application No. 09/620,652, filed on Jul. 20, 2000, now Pat. No. 6,713,077.

(60) Provisional application No. 60/146,083, filed on Jul. 28, 1999.

(51) Int. Cl.
*A01N 25/26* (2006.01)

(52) U.S. Cl.
USPC .......................................... 504/100

(58) Field of Classification Search
None
See application file for complete search history.

(56) References Cited

U.S. PATENT DOCUMENTS

| 4,272,276 | A |   | 6/1981 | Szejtli et al. ............... 71/76 |
| 4,780,279 | A | * | 10/1988 | Enos ............................... 422/32 |
| 5,696,144 | A |   | 12/1997 | Royalty et al. ............... 514/404 |
| 5,849,320 | A |   | 12/1998 | Turnblad et al. ............... 424/410 |
| 5,876,739 | A | * | 3/1999 | Turnblad et al. ............... 424/408 |
| 5,877,012 | A |   | 3/1999 | Estruch et al. ............. 435/252.3 |
| 5,950,360 | A |   | 9/1999 | Heinrich et al. ............... 47/58.1 |
| 6,660,690 | B2 | * | 12/2003 | Asrar et al. .................. 504/100 |
| 6,713,077 | B1 | * | 3/2004 | Kohn ............................ 424/405 |
| 6,903,093 | B2 | * | 6/2005 | Asrar et al. ............... 514/229.2 |
| 2005/0124492 | A1 |   | 6/2005 | Asrar et al. .................. 504/100 |
| 2005/0148470 | A1 |   | 7/2005 | Asrar et al. .................. 504/100 |

FOREIGN PATENT DOCUMENTS

| DE | 4220931 A1 | 5/1994 |
| DE | 4220931 A1 | 5/1994 |
| EP | 0091213 A2 | 12/1983 |
| GB | 2333043 A | 7/1999 |
| GB | 2333043 A | 7/1999 |
| HU | P8301144 A | 4/1983 |
| WO | 95/31889 | 11/1995 |
| WO | WO 95/31889 | 11/1995 |
| WO | WO 99/09830 | 3/1999 |
| WO | WO 99/09830 | 4/1999 |
| WO | 01/08490 A1 | 2/2001 |

OTHER PUBLICATIONS

Graham-Bryce, I.J., et al., Interactions of Pyrimidine Fungicides With Soil and Their Influence on Uptake by Plants, in Proc. 6th Br. Insectic. Fungic. Conf., pp. 419-430, (1971).
Abstract XP002153171, Abstract of JP8280210 to Nissan Chem Ind Ltd, Published Oct. 29, 1996.
Abstract XP000943435, Gouger, et al., BCPD, Pests and Diseases, 3:1143-1150 (1986).
Gatehouse et al., Behavior of permethrin as a seed treatment against larvae of the wheat bulb fly, Pesticide Science, 1982, vol. 13 No. 2, 109-18.
Maskell et al (Chemical control of wheat bulb fly attaching winter wheat in eastern England, Annals of Applied Biology, 1986, 109 (2), 223-236.ABS.
European Patent Office, International Search Report, completed Nov. 17, 2000, mailed Dec. 13, 2000, International Application No. PCT/US00/20004, International Filing Date Jul. 21, 2000, Monsanto Company.
Zeneca AG Products, Force 3G Insecticide, brochure, Sep. 3605-010 R2 7/98, 5 pages.
L V. Edgington, et al., Chapter 2 Systemic Fungicides: Theory, Uptake, and Translocation, Department of Environmental Biology, University of Guelph, Guelph, Ontario, Canada, pp. 51-89, pub. 1977.
Zeneca AG Products, Zeneca Inc., Force 30 CS—Container FOR397. rsb—070996,Material Safety Data Sheet, marked as received at EPA Jul. 16, 1996, pp. 1-6.
Nu-Gro Raze, brochure, Wilbur Ellis Company, 2 pages.
Warrior T Insecticide with Zeon Technology, Zeneca AG Products, brochure, 09-2590-065 R1 8/98, 12 pages.
Hungarian Patent Office, Office Action dated Dec. 16, 2011, Hungarian Patent Application No. p. 02 02240—National phase of PCT/US 00/20004, Monsanto Technology LLC.
Brazillian Patent and Trademark Office, Office Action, dated Jan. 19, 2012, Brazillian Patent Application No. PI0012781-7, filed Jul. 21, 2000, Applicant: Monsanto Technology LLC.
Hungarian Patent Office, Hungarian Novelty Search Report, dated Nov. 15, 2002, Hungarian Application No. P0202240 (National Hungarian Phase of PCT/US00/20004).
Zeneca AG Products, Force 3G Insecticide, brochure, 09-3605-010 R2, dated Jul. 1998, 5 pages.
Warrior T Insecticide with Zeon Technology, Zeneca AG Products, brochure, 09-2590-065 R1, dated Aug. 1998, 12 pages.
Singh et al., Indian Journal of Agricultural Sciences, 58(10): 783-785 (Oct. 1988).

* cited by examiner

*Primary Examiner* — Alton Pryor
(74) *Attorney, Agent, or Firm* — Nelson Mullins Riley & Scarborough, LLP

(57) ABSTRACT

A method of preventing damage to the shoots and foliage of a plant by a pest includes treating a seed having an exogenous gene that encodes for the production of a protein having activity against European corn borer or corn root worm with a composition comprising at least one pyrethrin or synthetic pyrethroid that is selected on the basis of having an activity against an insect other than European corn borer or corn root worm. Treated seeds are also provided.

40 Claims, No Drawings

CONTROL OF SHOOT/FOLIAR FEEDING PESTS WITH PESTICIDE SEED TREATMENTS

CROSS-REFERENCE TO RELATED PATENTS AND PATENT APPLICATIONS

This application is a continuation of U.S. patent application Ser. No. 10/658,923, filed Sep. 9, 2003, which was a continuation of U.S. patent application Ser. No. 09/620,652, filed Jul. 20, 2000, which issued on Mar. 30, 2004 as U.S. Pat. No. 6,713,077, which claimed priority to U.S. Provisional Patent Application Ser. No. 60/146,083, filed Jul. 28, 1999, each of which is incorporated by reference herein in its entirety.

BACKGROUND OF THE INVENTION (1) Field of the Invention

This invention relates generally to the control of plant pests and more particularly to pesticidal seed treatments which provide protection against pest feeding damage to above ground plant parts.

(2) Description of the Related Art

The control of insects and related arthropods is of extreme importance to the agricultural industry. Every year, these pests destroy an estimated 15% of agricultural crops in the United States and even more than that in developing countries. Some of this damage occurs in the soil when plant pathogens, insects and other such soil borne pests attack the seed after planting. Much of the rest of the damage is caused by rootworms; plant pathogens that feed upon or otherwise damage the plant roots; and by cutworms, European corn borers and other pests that feed upon or damage the above ground parts of the plant. General descriptions of the type and mechanisms of attack of pests on agricultural crops are provided by, for example, Metcalf, in *Destructive and Useful Insects*, (1962); and Agrios, in *Plant Pathology*, 3rd Ed., Academic Press (1988).

The period during germination of the seed, sprouting and initial growth of the plant is particularly critical because the growing plant is small and even a small amount of damage can cause the loss of the entire plant. Moreover, some natural plant defenses are not fully developed at this stage and the plant is vulnerable to attack. Not surprisingly, the control of pests that attack above ground plant parts during this early stage of plant growth is a well developed area of agriculture.

Currently, the control of pests that attack post emergent crops primarily involves the application of synthetic organic pesticides to the soil, or to the growing plants by foliar spraying. Because of concern about the impact of chemical pesticides on public health and the environment, there has been much effort to reduce the amount of chemical pesticides that are used. A significant portion of this effort has been expended in developing transgenic crops engineered to express insect toxicants from microorganisms. For example, U.S. Pat. No. 5,877,012 to Estruch et al. discloses the cloning and expression of proteins from such organisms as *Bacillus, Pseudomonas, Clavibacter* and *Rhizobium* into plants to obtain transgenic plants with resistance to such pests as black cutworms, armyworms, several borers and other insect pests. Publication WO/EP97/07089 by Privalle et al. teaches the transformation of monocotyledons, such as corn, with a recombinant DNA sequence encoding peroxidase for the protection of the plant from feeding by corn borers, earworms and cutworms. Jansens et al., in *Crop Sci.*, 37(5):1616-1624 (1997), reported the production of transgenic corn containing a gene encoding a crystalline protein from *Bacillus thuringiensis* that controlled both generations of the European corn borer. U.S. Pat. Nos. 5,625,136 and 5,859,336 to Koziel et al. reported that the transformation of corn with a gene from *B. thuringiensis* that encoded for delta-endotoxins provided the transgenic corn with improved resistance to European corn borer.

A comprehensive report of field trials of transgenic corn that expresses an insecticidal protein from *B. thuringiensis* has been provided by Armstrong et al., in *Crop Science*, 35(2):550-557 (1995).

At the present state of plant cellular engineering, however, transgenic crops are typically resistant only to specific pests for that crop, e.g., transgenic corn expressing a Bt toxin against the corn rootworm. It is frequently necessary to apply synthetic pesticides to such transgenic plants to control damage by other pests.

Insecticides such as synthetic pyrethroids, organophosphates and carbamates; fungicides such as azoles and anilopyrimidines; and acaricides such as pyrazoles; and the like, are very effective against certain above ground plant pests when applied at the proper time and with proper procedures. Appropriate pesticides may be applied at the time of planting as surface bands, "T"-bands, or in-furrow, but these applications require the additional operation of applying the pesticide at the same time as the seeds are being sown. This complicates the planting operation and the additional equipment required for pesticide application is costly to purchase and requires maintenance and attention during use. Moreover, care must be taken to incorporate the pesticides properly into the topmost soil layer for optimal activity. (See, for example, the brochure titled *Force* 3G *Insecticide*, published by Zeneca Ag Products, Wilmington, Del. (1998)).

The activity of pesticides that have been applied as in-furrow applications at the time of sowing is usually limited to protection of the seed or the roots of the plant. Some protection against above ground pests such as corn borers has been reported, however, for such treatments with insecticides known to be systemic. Keaster and Fairchild, *J. Econ. Entomol.*, 61(2):367-369 (1968). Since such pesticide chemicals are complex molecules that are expensive to produce, purchase and use, it is desirable that their activity is not diluted or lost by migration away from the desired site of action by moisture seepage or by vaporization.

After the plant has emerged from the soil, foliar spraying of pesticides is often used to control those pests that attach the shoots and foliage of the plant. However, a foliar spray must be applied at a certain time that coincides with the presence and activity of the pest in order to have the most beneficial effect. Application at this time may be difficult or impossible if, for example, weather conditions limit access to the field. Moreover, the plants must be monitored closely to observe early signs of pest activity in order to apply the pesticide at a time when the pests are most vulnerable.

Synthetic pyrethroids have been found to give excellent control of *Lepidopteran* sp. pests such as cutworms when applied as foliar spray or as surface-incorporated granules at the time of planting. However, since this class of insecticides has very high toxicity to fish, for example, great care must be taken to limit the runoff of the insecticide from either granules or spray into surface waters. Moreover, any foliar spraying must be done at times when there is little wind, and then only with proper equipment that is carefully monitored during use.

The control of pests by applying insecticides directly to plant seed has also been described. For example, U.S. Pat. No. 5,696,144 discloses that the European corn borer caused less feeding damage to corn plants grown from seed treated with a 1-arylpyrazole compound at a rate of 500 g per quintal of seed than control plants grown from untreated seed. In addition, U.S. Pat. No. 5,876,739 to Turnblad et al., (and its parent, U.S. Pat. No. 5,849,320) disclose a method for controlling soil-borne insects which involves treating seeds with a coating containing one or more polymeric binders and an insecticide. This reference provides a list of insecticides that it identifies as candidates for use in this coating and also names a number of potential target insects. However, while the U.S. Pat. No. 5,876,739 patent states that treating corn seed with a coating containing a particular insecticide protects corn roots from damage by the corn rootworm, it does not indicate or otherwise suggest that treatment of corn seed with insecticides, and in particular, with water insoluble, non-volatile chemicals, such as most pyrethroids, provided protection to the shoot and/or foliage of the resulting corn plants. Moreover, neither the U.S. Pat. No. 5,696,144 patent nor the U.S. Pat. No. 5,876,739 patent disclosed treating transgenic corn seed or other transgenic plant seeds with insecticides to provide protection against insect feeding damage to the shoots and foliage of the resulting transgenic plant.

Thus, although the art of protecting the shoots and foliage—as well as the seed and roots—of a plant from damage by pests has been advancing rapidly, several problems still remain. For example, it would be useful to provide a method for the control of pest damage to shoots and foliage of plants without the requirement of applying a pesticide at the time of sowing the seed, and in addition to sowing the seed, either as a surface incorporated band, or in-furrow, for example, or requiring a later field application of a pesticide during plant growth. It would also be useful if the method for pest control minimized the danger of pesticide runoff and minimized the migration of the pesticide from the desired zone of activity by moisture seepage or by vaporization. Furthermore, it would be useful if such a method could be coupled with the biopesticidal activity of transgenic plants to selectively broaden the scope of protection that is provided for the shoots and foliage of the resulting transgenic plant.

SUMMARY OF THE INVENTION

Briefly, therefore, the present invention is directed to a novel method of preventing damage by a pest to shoots and foliage of a plant grown from a seed, the method comprising treating the seed from which the plant grows with a composition comprising at least one insecticide selected from the group consisting of pyrethrin and synthetic pyrethroids.

The present invention is also directed to a novel seed having adhered thereto at least one pyrethrin or synthetic pyrethroid having activity against at least one pest in an amount effective to provide protection to the shoots and foliage of the plant against damage by the at least one pest.

The present invention is also directed to a novel method of preventing damage to the shoots and foliage of a plant by a cutworm, the method comprising treating the seed from which the plant grows with a composition comprising at least one water insoluble and non-volatile insecticide in an amount effective to prevent damage to the shoots and foliage of the plant by a cutworm.

The present invention is also directed to a novel method of protecting a transgenic plant against damage by multiple pests, the method comprising treating a seed from which the transgenic plant grows, which seed has at least one heterologous gene encoding for the expression of a protein that is active against a first pest, with a composition comprising at least one pesticide having activity against at least one second pest.

The present invention is also directed to a novel transgenic seed from which a transgenic plant grows, which seed has at least one heterologous gene encoding for the expression of a protein that is active against a first pest, the seed having adhered thereto at least one pesticide having activity against at least one second pest in an amount sufficient to provide protection to the transgenic plant against damage by the at least one second pest.

The present invention is also directed to a seed that is protected against multiple pests comprising a seed having at least one heterologous gene encoding for the expression of a protein that is active against a first pest and, in addition, at least one pesticide in an amount effective to provide protection to the shoots and foliage of the plant against damage by at least one second pest.

Among the advantages found to be achieved by the present invention, therefore, may be noted the provision of a method for the control of pest damage to shoots and foliage of plants without the requirement of applying a pesticide at the time of sowing the seed, and in addition to sowing the seed, either as a surface incorporated band, or in-furrow, for example, or requiring a later field application of a pesticide during plant growth; the provision of a method for pest control that minimizes the danger of pesticide runoff and minimizes the migration of the pesticide from the desired zone of activity by moisture seepage or by vaporization; and the provision of method that can be coupled with the biopesticidal activity of transgenic plants to selectively broaden the scope of protection that is provided for the shoots and foliage of the transgenic.

DETAILED DESCRIPTION OF THE PREFERRED EMBODIMENTS

In accordance with the present invention, it has been discovered that treatment of seeds with pyrethrins or synthetic pyrethroids not only protects the seeds themselves, but—surprisingly—also provides post-emergent control of pests that feed on or otherwise damage the shoots and/or foliage of the plant. While pyrethroids are mentioned in its laundry list of candidates for seed protection, U.S. Pat. No. 5,876,739 nowhere provides any suggestion that such pesticides provide such a surprising and unpredictable advantage with respect to the protection of the shoots and foliage of the resulting plants. Moreover, it has been discovered that a similar treatment can be applied to the seeds of transgenic plants, using almost any pesticide, but particularly those that are water insoluble and non-volatile, with the result that the pesticide treatment of the seed provides protection of the shoots and foliage of the transgenic plant after emergence from damage by pests against which the pesticide is active. In particular, it has been found that the treatment of corn seed with certain insecticides, in particular with synthetic pyrethroids such as lambda-cyhalothrin, results in protection of plant shoots and foliage against feeding damage by black cutworm larvae. In fact, the novel treatment was found to provide a degree of protection that was at least equal to that provided by the currently recognized standard commercial treatment. This discovery was unexpected because lambda-cyhalothrin and most other pyrethroids reportedly have extremely low water solubility, as well as low volatility, and are believed to be non-systemic in their mode of action. See, e.g., *The Pesticide Manual*, 11th Ed., British Crop Protection Council, 1997. Indeed, the scientific literature indicates that tefluthrin is unique among pyrethroid actives in its inherent level of systemicity from a soil application. See, e.g., *Agricultural Chemicals, Book 1 Insecticides*, pp. 92-93, 14th Ed., W. T. Thompson, Ed., Thompson Publ., Fresno, Calif. (1998). However, seed treatment formulations of tefluthrin are labeled only for wireworms and the labels do not suggest activity against pests attacking plant shoots and foliage after sprouting. (See, e.g., the specification sheet for Nu-Gro® RAZE, Wilbur-Ellis Co., San Francisco, Calif. (no date)). On the other hand, lambda cyhalothrin, and essentially all other synthetic pyrethroids are well known for the control of above ground pests, but only when used as foliar sprays or surface-incorporated preparations. (See, e.g., the product bulletin for WARRIOR® T insecticide, available from Zeneca Ag Products, Wilmington, Del. (1998)).

Thus, prior to the present discovery, the skilled artisan would not have predicted that pyrethrin or synthetic pyrethroids as a class would have significant activity against pests that damage plant shoots and foliage when applied as a seed treatment. Based on the results reported herein, it is believed that a wide range of pyrethroids and other insecticides, and especially including those having low water solubility, low volatility and previously considered to be "non-systemic", are capable of providing protection against shoot/foliar feeding pests.

It is also believed that the novel treatment can be used with transgenic seeds of the type having a heterologous gene encoding for the expression of a pesticidal protein in the transgenic plant that grows from the seed. Treating such a seed with a pesticide would provide the ability to protect against one pest with the transgenicity and against another, perhaps different, pest with the pesticide treatment.

Pesticides suitable for use in the invention include compounds selected from azoles, azines, pyrethrins, pyrethroids, organophosphates, caramoyloximes, pyrroles, pyrazoles, pyridines, amidines, halogenated hydrocarbons and carbamates and combinations and derivatives thereof. Known pesticides within these categories are listed in *The Pesticide Manual,* 11th Ed., C. D. S. Tomlin, Ed., British Crop Protection Council, Farnham, Surry, UK (1997). The skilled artisan can readily determine whether a particular compound, when applied to seeds, is able to exert a pesticidal effect on a target pest that feeds on plant shoots and foliage. When the term "pesticide" is used herein, it is not meant to include pesticides that are produced by the particular seed or the plant that grows from the particular seed that is treated with the pesticide.

As used herein, the terms "pesticidal effect" and "pesticidal activity" mean any direct or indirect action on the target pest that results in reduced feeding damage on the shoots and foliage of plants grown from treated seeds as compared to plants grown from untreated seeds. The terms "active against a (first or second) pest", also have the same meaning. Such direct or indirect actions include inducing death of the pest, repelling the pest from the plant shoots and/or foliage, inhibiting feeding of the pest on or the laying of its eggs on the plant shoots and/or foliage, and inhibiting or preventing reproduction of the pest. As used herein, the "shoots and foliage" of a plant are to be understood to be the shoots and leaves of the plant after the seed has sprouted, but not including the roots of the plant. It is preferable that the shoots and foliage of a plant be understood to be those non-root parts of the plant that have grown from the seed and are located a distance of at least one inch away from the seed from which they emerged (outside the region of the seed), and more preferably, to be the non-root parts of the plant that are at or above the surface of the soil. As used herein, the "region of the seed" is to be understood to be that region within about one inch of the seed.

Pyrethroids are preferred for use as the pesticide in the present invention. The pyrethroids that are preferred include pyrethrins and synthetic pyrethroids. The pyrethrins that are preferred for use in the present method include, without limitation, 2-allyl-4-hydroxy-3-methyl-2-cyclopenten-1-one ester of 2,2-dimethyl-3-(2methyl propenyl)-cyclopropane carboxylic acid, and/or (2-methyl-1-propenyl)-2-methoxy-4-oxo-3-(2 propenyl)-2-cyclopenten-1-yl ester and mixtures of cis and trans isomers thereof.

Synthetic pyrethroids that are preferred for use in the present invention include (s)-cyano(3-phenoxyphenyl)methyl 4-chloro alpha (1-methylethyl)benzeneacetate (fenvalerate); (S)-cyano (3-phenoxyphenyl)methyl (S)-4-chloro-alpha-(1-methylethyl)benzeneacetate (esfenvalerate); (3-phenoxyphenyl)-methyl(+)cis-trans-3-(2,2-dichoroethenyl)-2,2-dimethylcyclopropanecarboxylate (permethrin); (±) alpha-cyano-(3-phenoxyphenyl)methyl(+)-cis,trans-3-(2,2-dichloroethenyl)-2,2-dimethyl-cyclopropane carboxylate (cypermethrin); (beta-cypermethrin); (theta cypermethrin); S-cyano (3-phenoxyphenyl)methyl (±) cis/trans 3-(2,2-dichloroethenyl) 2,2 dimethylcyclopropane carboxylate (zeta-cypermethrin); (s)-alpha-cyano-3-phenoxybenzyl (IR, 3R)-3-(2,2-dibromovinyl)-2,2-dimethyl cyclopropanecarboxylate (deltamethrin); alpha-cyano-3-phenoxybenzyl 2,2, 3,3,-tetramethyl cyclopropoanecarboxylate (fenpropathrin); (RS)-alpha-cyano-3-phenoxybenzyl(R)-2-[2-chloro-4-(trifluoromethyl)anilino]-3-methylbutanoate (tau-fluvalinate); (2,3,5,6-tetrafluoro-4-methylphenyl)-methyl-(1 alpha,3 alpha)-(Z)-(±)-3-(2-chloro-3,3,3-trifluoro-1-propenyl)-2,2-dimethylcyclopropanecarboxylate (tefluthrin); (±)-cyano (3-phenoxyphenyl)methyl (±)-4-(difluoromethoxy)-alpha-(1-methyl ethyl)benzeneacetate (flucythrinate); cyano(4-fluoro-3-phenoxyphenyl)methyl 3-[2-chloro-2-(4-chlorophenyl)ethenyl]-2,2-dimethylcyclopropanecarboxylate (flumethrin); cyano(4-fluoro-3-phenoxyphenyl)methyl 3-(2, 2-dichloroethenyl)-2,2-dimethyl-cyclopropanedarboxylate (cyfluthrin); (beta cyfluthrin); (transfluthrin); (S)-alpha-cyano-3-phenoxybenzyl(Z)-(IR-cis)-2,2-dimethyl-3-[2-(2,2,2-trifluoro-trifluoromethyl-ethoxycarbonyl)vinyl]cyclopropane carboxylate (acrinathrin); (IR cis) S and (IS cis) R enantiomer isomer pair of alpha-cyano-3-phenoxybenzyl-3-(2,2-dichlorovinyl)-2,2-dimethylcyclopropane carboxylate (alphacypermethrin); [IR,3S)3(1'RS)(1',2',2',2'-tetrabromoethyl)]-2,2-dimethyl cyclopropanecarboxylic acid (s)-alpha-cyano-3-phenoxybenzyl ester (tralomethrin); cyano-(3-phenoxyphenyl)methyl 2,2-dichloro-1-(4-ethoxyphenyl) cyclopropane carboxylate (cycloprothrin); [1α,3α(Z)]-(±)-cyano-(3-phenoxyphenyl)methyl 3-(2-chloro-3,3,3-trifluoro-1-propenyl)-2,2-cimethylcyclopropanecarboxylate (cyhalothrin); [1 alpha(s),3 alpha(z)]-cyano(3-phenoxyphenyl)methyl-3-(2-chloro-3,3,3-trifluoro-1-propenyl)-2,2-dimethylcyclopropane carboxylate (lambda cyhalothrin); (2-methyl [1,1'-biphenyl]-3-yl)methyl 3-(2-chloro-3,3,3-trifluoro-1-propenyl)-2,2-dimethyl-cyclopropanecarboxylate (bifenthrin); 5-1-benzyl-3-furylmethyl-d-cis(1R,3S,E)2,2-dimethyl-3-(2-oxo,-2,2,4,5 tetrahydro thiophenylidenemethyl)cyclopropane carboxylate (kadethrin, RU15525); [5-(phenyl methyl)-3-furanyl]-3-furanyl 2,2-dimethyl-3-(2-methyl-1-propenyl)cyclopropane carboxylate (resmethrin); (1R-trans)-[5-(phenylmethyl)-3-furanyl]methyl 2,2-dimethyl-3-(2-methyl-1-propenyl)cyclopropanecarboxylate (bioresmethrin); 3,4,5,6-tetrahydro-phthalimidomethyl-(IRS)-cis-trans-chrysanthemate (tetramethrin); 3-phenoxybenzyl-d,l-cis,trans 2,2-dimethyl-3-(2-methylpropenyl)cyclopropane carboxylate (phenothrin); (empenthrin); (cyphenothrin); (prallethrin); (imiprothrin); (RS)-3-allyl-2-methyl-4-oxcyclopent-2-enyl-(1A,3R;1R,3S)-2,2-dimethyl-3-(2-methylprop-1-enyl)cyclopropane carboxylate (allethrin); (bioallethrin); and (ZXI8901). It is believed that mixtures of one or more of the aforementioned synthetic pyrethroids can also be used in the present invention.

In one embodiment of the present invention, particularly preferred synthetic pyrethroids are tefluthrin, lambda cyhalothrin, bifenthrin, permethrin and cyfluthrin. Even more preferred synthetic pyrethroids are tefluthrin and lambda cyhalothrin. In another embodiment of the invention—that is described below—the preferred synthetic pyrethroids are selected according to volatility and water solubility.

One embodiment of this invention comprises the treatment of a transgenic seed with a pesticide. When the transgenic seed has at least one heterologous gene encoding for the expression of a protein that is active against a first pest, the seed can be treated with at least one pesticide having activity against at least one second pest. The present method can be used when first pest and the second pest are the same, for the purpose, for example, to obtain effective control of a particularly resistant or highly damaging pest. But in a separate embodiment, the transgenic trait protects the seed and/or plant from a first pest and the pesticide is selected to control a second pest that is different from the first pest. This method is particularly advantageous when an expressed transgenic gene provides a gene product that can protect a transgenic plant from one pest, but has no activity from a second, different pest. In this case, a pesticide can be selected that has activity against the second pest, thus providing the seed and plant with protection from both pests. By way of explanation, when a "first" pest and a "second" pest are referred to herein, it should be understood that each of the terms can include only one pest, or can include two or more pests.

In the embodiment in which a pesticide is applied to a transgenic seed, pesticides suitable for use include nematocides, insecticides, fungicides and acaricides. Compounds having suitable activity can be selected from azoles, azines, pyrethrins, pyrethroids, organophosphates, caramoyloximes, pyrroles, pyrazoles, pyridines, amidines, halogenated hydrocarbons and carbamates and combinations and derivatives thereof. Although any such pesticide or mixture thereof can be used, it is believed that pesticides that are water-insoluble and non-volatile are preferred.

When it is said that a pesticide is water-insoluble, it is meant that the pesticide has a water solubility that is sufficiently low to prevent the leaching of the pesticide away from a seed, or from the region of the seed, for at least about 12 days after the seed sprouts, by the solvent action of soil moisture, as caused, for example, by rain or irrigation, so as to reduce the level of the pesticide in or on the seed to below about one-half of the amount that was present in or on the seed at the time of planting. It is preferred that the pesticide has a water solubility of less than 100 mg/l at 20° C.; more preferred of less than 10 mg/l; even more preferred of less than 5 mg/l; even more preferred of less than 1 mg/l; even more preferred of less than 0.1 mg/l; even more preferred of less than 0.018 mg/l; and yet more preferred of less than 0.01 mg/l, all at 20° C. When it is said that a pesticide is non-volatile it is meant that the pesticide has a volatility that is sufficiently low to prevent the loss by evaporation of the pesticide away from a seed, or the region of the seed, for at least about 12 days after the seed sprouts, so as to reduce the level of the pesticide in or on the seed to below about one-half of the amount that was present in or on the seed at the time of planting. It is preferred that the pesticide has a volatility (expressed as vapor pressure) of less than 50 mPa at 20° C.; more preferred of less than 10 mPa; even more preferred of less than 6 mPa; and yet more preferred of less than 1 mPa, all at 20° C.

It is believed that the combination of low water solubility and low vapor pressure contribute to the particular advantage of the present method that loss of the treating pesticide by being leached away from the seed by water or removed from the seed by evaporation is minimized. It has been found that pyrethroids are particularly preferred for this embodiment, because of their low water solubility and low volatility as a class. For example, in Table 1, the water solubility and vapor pressure of pyrethrins and a number of synthetic pyrethroids is provided.

TABLE 1

Systemic activity and selected physical properties of pyrethrins and synthetic pyrethroids.[a]

| Pyrethrin and Synthetic Pyrethroids | Systemicity | Water solubility | Vapor pressure |
|---|---|---|---|
| Pyrethrins | non-systemic | 0.2-9 ppm | 5.3E–2 to 2.7 mPa[c] |
| Acrinathrin | n/a | 0.02 mg/l (25° C.) | 4.4E–5 mPa |
| Allethrin | non-systemic | practically insol. | 0.16 mPa (21° C.) |
| Alpha cypermethrin | non-systemic | 0.01 mg/l (25° C.) | 2.3E–2 mPa |
| Beta cyfluthrin | non-systemic | 1.2-2.1 μg/l (25° C.) | 1.4 to 8.5E–5 |
| Beta-cypermethrin | non-systemic | 93.4 μg/l (25° C.) | 1.8E–4 mPa |
| Bifenthrin | n/a | 0.1 mg/l | 0.024 mPa (25° C.) |
| Bioallethrin | non-systemic | 4.6 mg/l | 43.9 mPa (25° C.) |
| Bioresmethrin | n/a | <0.3 mg/l | 18.6 mPa (Tech.); 0.45 mPa (d-resmethrin) |
| Cycloprothrin | n/a | 0.091 mg/l (25° C.) | 2.13E–3 mPa (20° C.) |
| Cyfluthrin | non-systemic | 2-4.3 μg/l (25° C.) | 1.4E–4 to 19.6E–4 |
| Cyhalothrin | non-systemic | 0.004 ppb (20° C.) | 0.001 mPa |
| Cypermethrin | non-systemic | 0.004 mg/l (20° C.) | 2.3E–4 mPa |
| Cyphenothrin | non-systemic | <10 μg/l (25° C.) | 0.12 mPa (20° C.) |
| Deltamethrin | non-systemic | <0.2 μg/l (25° C.) | 1.24E–5 mPa |
| Empenthrin | n/a | 0.111 mg/l | 14 mPa (23.6° C.) |
| Esfenvalerate | n/a | 0.002 mg/l | 2E–4 mPa |
| Fenpropathrin | n/a | 14.1 μg/l (25° C.) | 0.73 mPa |
| Fenvalerate | non-systemic | <10 μg/l | 1.92E–2 mPa (20° C.) |
| Flucythrinate | non-systemic | 0.5 mg/l (21° C.) | 0.0012 mPa (25° C.) |
| Flumethrin | non-systemic | n/a | n/a |
| Imiprothrin | n/a | 93.5 mg/l | 1.8E–3 mPa (25° C.) |
| Kadethrin (RU15525) | n/a | practically insol. | <0.1 mPa (20° C.) |
| Lambda cyhalothrin | non-systemic | 0.005 mg/l | 2E–4 mPa |
| Permethrin | non-systemic | 0.2 mg/l (30° C.) | 0.07 mPa |
| Phenothrin | non-systemic | <9.7 μg/l (25° C.) | 1.9E–2 mPa (21.4° C.) |
| Prallethrin | n/a | 8 mg/l | <0.013 mPa (23.1° C.) |
| Resmethrin | non-systemic | 37.9 μg/l (25° C.) | <0.01 mPa (25° C.) |
| Tau-fluvalinate | n/a | 1.03 ppb (20° C.) | 9E–8 mPa |
| Tefluthrin | systemic[b] | 0.02 mg/l (20° C.) | 8 mPa (20° C.) |
| Tetramethrin | non-systemic | 1.83 mg/l | 0.944 mPa (30° C.) |
| Theta cypermethrin | n/a | 114.6 μg/l (25° C.) | 1.8E–4 mPa |
| Tralomethrin | non-systemic | 80 μg/l | 4.6E–6 mPa (25° C.) |
| Transfluthrin | n/a | 5.7E–5 g/l (20° C.) | 0.4 mPa |
| Zeta-cypermethrin | n/a | 0.045 mg/l (25° C.) | 2.5E–4 mPa |
| ZXI8901 | n/a | 3.56 μg/l | 1.6E–4 mPa (20° C.) |

[a]All data from: *The Pesticide Manual*, Eleventh Edition, C. D. S. Tomlin, Ed., British Crop Protection Council, Farnham, Surry, UK (1997), except as noted.
[b]From *Agricultural Chemicals, Book 1Insecticides*, 14th Edition, W. T. Thompson, Ed., Thompson Publications, Fresno, CA (1998).
[c]The term "E–y", means the same as × $10^{-y}$. For example, 2.5E–4 means $2.5 \times 10^{-4}$.

Table 1 also shows that the systemic activity of these insecticides is almost uniformly reported to be nonexistent with the possible exception of tefluthrin. It is also noted that tefluthrin has somewhat higher water solubility and, in particular, higher vapor pressure than most of the other pyrethroids. Without wishing to be bound by this or any other theory, the inventors believe that the combination of the level of water solubility, vapor pressure and specific activity of tefluthrin upon certain insect species results in the report of this chemical as having some degree of systemic activity. In one embodiment of the present invention, it is preferred to use insecticides, and in particular, pyrethrins and synthetic pyrethroids, other than tefluthrin.

In another embodiment of the present invention, it is preferred to use insecticides, and in particular, pyrethrins and synthetic pyrethroids that have a water solubility or a vapor pressure that is lower than that of tefluthrin. It is believed that such insecticides provide the benefit of very low movement away from the region of the seed and maintain high levels of protective activity for the shoots and foliage of the plant while minimizing the pollution of groundwater and the surrounding environment. Namely, such preferred insecticides have a water solubility that is less than about 0.02 mg/l (20° C.) and/or a vapor pressure of less than about 8 mPa (20° C.). More preferably, such preferred insecticides have a water solubility that is less than about 0.015 mg/l (20° C.) and/or a vapor pressure of less than about 6 mPa (20° C.).

Even more preferred insecticides include (s)-cyano(3-phenoxyphenyl)methyl 4-chloro alpha (1-methylethyl)benzeneacetate (fenvalerate); (S)-cyano (3-phenoxyphenyl)methyl (S)-4-chloro-alpha-(1-methylethyl)benzeneacetate (esfenvalerate); (3-phenoxyphenyl)-methyl(+)cis-trans-3-(2,2-dichoroethenyl)-2,2-dimethylcyclopropanecarboxylate (permethrin); (±) alpha-cyano-(3-phenoxyphenyl)methyl(+)-cis, trans-3-(2,2-dichloroethenyl)-2,2-dimethyl-cyclopropane carboxylate (cypermethrin); (beta-cypermethrin); (theta cypermethrin); S-cyano (3-phenoxyphenyl)methyl (±) cis/trans 3-(2,2-dichloroethenyl) 2,2 dimethylcyclopropane carboxylate (zeta-cypermethrin); (s)-alpha-cyano-3-phenoxybenzyl (IR,3R)-3-(2,2-dibromovinyl)-2,2-dimethyl cyclopropanecarboxylate (deltamethrin); alpha-cyano-3-phenoxybenzyl 2,2,3,3,-tetramethyl cyclopropoanecarboxylate (fenpropathrin); (RS)-alpha-cyano-3-phenoxybenzyl (R)-2-[2-chloro-4-(trifluoromethyl)anilino]-3-methylbutanoate (tau-fluvalinate); (±)-cyano (3-phenoxyphenyl)methyl (±)-4-(difluoromethoxy)-alpha-(1-methyl ethyl)benzeneacetate (flucythrinate); cyano(4-fluoro-3-phenoxyphenyl)methyl 3-[2-chloro-2-(4-chlorophenyl)ethenyl]-2,2-dimethylcyclopropanecarboxylate (flumethrin); cyano(4-fluoro-3-phenoxyphenyl)methyl 3-(2,2-dichloroethenyl)-2,2-dimethyl-cyclopropanedarboxylate (cyfluthrin); (beta cyfluthrin); (transfluthrin); (S)-alpha-cyano-3-phenoxybenzyl(Z)-(IR-cis)-2,2-dimethyl-3-[2-(2,2,2-trifluoro-trifluoromethyl-ethoxycarbonyl)vinyl]cyclopropane carboxylate (acrinathrin); (IR cis) S and (IS cis) R enantiomer isomer pair of alpha-cyano-3-phenoxybenzyl-3-(2,2-dichlorovinyl)-2,2-dimethylcyclopropane carboxylate (alphacypermethrin); [IR,3S)3(1'RS)(1',2',2',2'-tetrabromoethyl)]-2,2-dimethyl cyclopropanecarboxylic acid (s)-alpha-cyano-3-phenoxybenzyl ester (tralomethrin); cyano-(3-phenoxyphenyl)methyl 2,2-dichloro-1-(4-ethoxyphenyl) cyclopropane carboxylate (cycloprothrin); [1α,3α(Z)]-(±)-cyano-(3-phenoxyphenyl)methyl 3-(2-chloro-3,3,3-trifluoro-1-propenyl)-2,2-cimethylcyclopropanecarboxylate (cyhalothrin); [1 alpha (s),3 alpha(z)]-cyano(3-phenoxyphenyl)methyl-3-(2-chloro-3,3,3-trifluoro-1-propenyl)-2,2-dimethylcyclopropane carboxylate (lambda cyhalothrin); (2-methyl [1,1'-biphenyl]-3-yl)methyl 3-(2-chloro-3,3,3-trifluoro-1-propenyl)-2,2-dimethyl-cyclopropanecarboxylate (bifenthrin); 5-1-benzyl-3-furylmethyl-d-cis(1R,3S,E)2,2-dimethyl-3-(2-oxo,-2,2,4,5 tetrahydro thiophenylidenemethyl)cyclopropane carboxylate (kadethrin, RU15525); [5-(phenyl methyl)-3-furanyl]-3-furanyl 2,2-dimethyl-3-(2-methyl-1-propenyl)cyclopropane carboxylate (resmethrin); (1R-trans)-[5-(phenylmethyl)-3-furanyl]methyl 2,2-dimethyl-3-(2-methyl-1-propenyl)cyclopropanecarboxylate (bioresmethrin); 3,4,5,6-tetrahydro-phthalimidomethyl-(IRS)-cis-trans-chrysanthemate (tetramethrin); 3-phenoxybenzyl-d,l-cis,trans 2,2-dimethyl-3-(2-methylpropenyl)cyclopropane carboxylate (phenothrin); (cyphenothrin); (prallethrin); (imiprothrin); (RS)-3-allyl-2-methyl-4-oxcyclopent-2-enyl-(1A,3R;1R,3S)-2,2-dimethyl-3-(2-methyl-prop-1-enyl)cyclopropane carboxylate (allethrin); and (ZXI8901). The most preferred insecticides for this embodiment are lambda cyhalothrin, bifenthrin, permethrin and cyflutrin. It is believed that mixtures of one or more of the aforementioned synthetic pyrethroids can also be used in the present invention.

It is contemplated that the present method can be used to protect the above-ground parts of field, forage, plantation, glasshouse, orchard or vineyard crops, ornamentals, plantation or forest trees. The seeds that are useful in the present invention can be the seeds of any species of plant. However, they are preferably the seeds of plant species that are agronomically important. In particular, the seeds can be of corn, peanut, canola/rapeseed, soybean, curcubits, crucifers, cotton, rice, sorghum, sugar beet, wheat, barley, rye, sunflower, tomato, sugarcane, tobacco, oats, as well as other vegetable and leaf crops. It is preferred that the seed be corn, soybeans, or cotton seed; and more preferred that the seeds be corn.

In one embodiment of the invention, as mentioned above, the seed is a transgenic seed from which a transgenic plant can grow. The transgenic seed of the present invention is engineered to express a desirable characteristic and, in particular, to have at least one heterologous gene encoding for the expression of a protein that is pesticidally active and, in particular, has insecticidal activity. The heterologous gene in the transgenic seeds of the present invention can be derived from a microorganism such as *Bacillus, Rhizobium, Pseudomonas, Serratia, Trichoderma, Clavibacter, Glomus, Gliocladium* and mycorrhizal fungi. In particular, it is believed that the present method would be especially beneficial when the heterologous gene is one that is derived from a *Bacillus* sp. microorganism and the protein is active against corn root worm. It is also believed that the present method would be especially beneficial when the heterologous gene is one that is derived from a *Bacillus* sp. microorganism and the protein is active against European corn borer. A preferred *Bacillus* sp. microorganism is *Bacillus thuringiensis*.

The target pest for the present invention is an adult or larvae of any insect or other pest that feeds on the shoots and foliage of the plant that is to be protected by the subject method. Such pests include but are not limited to cutworms (all species), thrips (all species), aphids (all species), cornstalk borers and other borers (all species), armyworm (all species), flea beetles (all species), mites (all species), chinch bugs (all species), stink bugs (all species), and grasshoppers (all species).

In one embodiment of the invention, a pesticide known to be active against the target pest is applied to a seed in an amount effective to provide protection to the shoots and foliage of the plant that grows from the seed. As used herein, "protection" is achieved if the percent of feeding damage to the shoots and foliage at 10 days after infestation (DAI) with the pest is reduced for plants grown from treated seeds as compared to plants grown from untreated seeds. It is preferred that the damage be reduced by a statistically significant amount; more preferably the seed treatment results in at least a 5% to 10% reduction in feeding damage; even more preferably, at least a 50% reduction in feeding damage; even more preferably, at least a 75% reduction and most preferably, treating the seeds in accordance with the invention substantially totally prevents damage to the plant shoots and foliage. When it is said that damage to the plant shoots and foliage is substantially totally prevented, it is meant that such damage is no higher than 5%.

The amount of pesticide that will provide protection to plant shoots and foliage will vary depending on the particular pesticide compound, the nature of the composition in which it is applied, the seed type, and the target pest. As used herein, an amount of the pesticide effective to provide protection to the shoots and foliage of the plant against damage by the pest is the lowest amount of such pesticide that will provide such protection. In general, the amount of pesticide used will range from about 0.005% to 25% of the weight of the seed, and more preferably, from about 0.01% to about 10%. A preferred range for pyrethroids is 0.01% to 1% of the active ingredient (AI) of the pyrethroids relative to the weight of the seed, and for corn seed treatment with lambda-cyhalothrin, a particularly preferred range is 0.1% to 0.5%.

In the present method, the pesticide is applied to a seed. Although it is believed that the present method can be applied to a seed in any physiological state, it is preferred that the seed be in a sufficiently durable state that it incurs no damage during the treatment process. Typically, the seed would be a seed that had been harvested from the field; removed from the plant; and separated from any cob, stalk, outer husk, and surrounding pulp or other non-seed plant material. The seed would preferably also be biologically stable to the extent that the treatment would cause no biological damage to the seed. In one embodiment, for example, the treatment can be applied to seed corn that has been harvested, cleaned and dried to a moisture content below about 15% by weight. In an alternative embodiment, the seed can be one that has been dried and then primed with water and/or another material and then re-dried before or during the treatment with the pesticide. Within the limitations just described, it is believed that the treatment can be applied to the seed at any time between harvest of the seed and sowing of the seed.

When it is said that a seed is "treated" with the pesticide, such treatment is not meant to include those practices in which the pesticide is applied to the soil, rather than to the seed. For example, such treatments as the application of the pesticide in bands, "T"-bands, or in-furrow, at the same time as the seed is sowed are not considered to be included in the present invention.

The pesticide can be applied "neat", that is, without any diluting or additional components present. However, the pesticide is typically applied to the seeds in the form of a pesticide composition. This composition may contain one or more other desirable components including but not limited to liquid diluents, binders to serve as a matrix for the pesticide, fillers for protecting the seeds during stress conditions, and plasticizers to improve flexibility, adhesion and/or spreadability of the coating. In addition, for oily pesticide compositions containing little or no filler, it may be desirable to add to the composition drying agents such as calcium carbonate, kaolin or bentonite clay, perlite, diatomaceous earth or any other adsorbent material. Use of such components in seed treatments is known in the art. See, e.g., U.S. Pat. No. 5,876,739. The skilled artisan can readily select desirable components to use in the pesticide composition depending on the seed type to be treated and the particular pesticide that is selected. In addition, readily available commercial formulations of known pesticides may be used, as demonstrated in the examples below.

The seeds may also be treated with one or more of the following ingredients: other pesticides, including compounds which act only below the ground; fungicides, such as captan, thiram, metalxyl, fludioxonil, oxadixyl, and isomers of each of those materials, and the like; herbicides, including compounds selected from carbamates, thiocarbamates, acetamides, triazines, dinitroanilines, glycerol ethers, pyridazinones, uracils, phenoxys, ureas, and benzoic acids; herbicidal safeners such as benzoxazine, benzhydryl derivatives, N,N-diallyl dichloroacetamide, various dihaloacyl, oxazolidinyl and thiazolidinyl compounds, ethanone, naphthalic anhydride compounds, and oxime derivatives; fertilizers; and biocontrol agents such as naturally-occurring or recombinant bacteria and fungi from the genera *Rhizobium, Bacillus, Pseudomonas, Serratia, Trichoderma, Glomus, Gliocladium* and mycorrhizal fungi. These ingredients may be added as a separate layer on the seed or alternatively may be added as part of the pesticide composition.

Preferably, the amount of pesticide or other ingredients used in the seed treatment should not inhibit generation of the seed, or cause phytotoxic damage to the seed.

The composition of the present invention can be in the form of a suspension; emulsion; slurry of particles in an aqueous medium (e.g., water); wettable powder; wettable granules (dry flowable); and dry granules. If formulated as a suspension or slurry, the concentration of the active ingredient in the composition is preferably about 0.5% to about 99% by weight (w/w), preferably 5-40%.

As mentioned above, other conventional inactive or inert ingredients can be incorporated into the composition. Such inert ingredients include but are not limited to: conventional sticking agents, dispersing agents such as methylcellulose (Methocel A15LV or Methocel A15C, for example, serve as combined dispersant/sticking agents for use in seed treatments), polyvinyl alcohol (e.g., Elvanol 51-05), lecithin (e.g., Yelkinol P), polymeric dispersants (e.g., polyvinylpyrrolidone/vinyl acetate PVPNA S-630), thickeners (e.g., clay thickeners such as Van Gel B to improve viscosity and reduce settling of particle suspensions), emulsion stabilizers, surfactants, antifreeze compounds (e.g., urea), dyes, colorants, and the like. Further inert ingredients useful in the present invention can be found in McCutcheon's, vol. 1, "*Emulsifiers and Detergents,*" MC Publishing Company, Glen Rock, N.J., U.S.A., 1996. Additional inert ingredients useful in the present invention can be found in McCutcheon's, vol. 2, "*Functional Materials,*" MC Publishing Company, Glen Rock, N.J., U.S.A., 1996.

The pesticides and compositions of the present invention can be applied to seeds by any standard seed treatment methodology, including but not limited to mixing in a container (e.g., a bottle or bag), mechanical application, tumbling, spraying, and immersion. Any conventional active or inert material can be used for contacting seeds with pesticides according to the present invention, such as conventional film-coating materials including but not limited to water-based film coating materials such as Sepiret (Seppic, Inc., Fairfield, N.J.) and Opacoat (Berwind Pharm. Services, Westpoint, Pa.).

The pesticide composition may be applied to the seeds using conventional coating techniques and machines, such as fluidized bed techniques, the roller mill method, rotostatic seed treaters, and drum coaters. Other methods, such as spouted beds may also be useful. The seeds may be presized before coating. After coating, the seeds are typically dried and then transferred to a sizing machine for sizing. Such procedures are known in the art.

The pesticide-treated seeds may also be enveloped with a film overcoating to protect the pesticide coating. Such overcoatings are known in the art and may be applied using conventional fluidized bed and drum film coating techniques.

If the pesticide is applied to the seed in the form of a coating, the seeds can be coated using a variety of methods including imbibition, solid matrix priming, coating, spraying and dusting. Seed treatments can take a variety of forms including, suspension concentrates, solutions, emulsions, powders and granules, as well as using polymeric carriers or stickers. For example, the coating process can comprise spraying a composition comprising the pesticide onto the seed while agitating the seed in an appropriate piece of equipment such as a tumbler or a pan granulator.

In one embodiment, when coating seed on a large scale (for example a commercial scale), typically seed is introduced into the treatment equipment (such as a tumbler, a mixer, or a pan granulator) either by weight or by flow rate. The amount of treatment composition that is introduced into the treatment equipment can vary depending on the seed weight to be coated, surface area of the seed, the concentration of the herbicide in the treatment composition, the desired concentration on the finished seed, and the like. The treatment composition can be applied to the seed by a variety of means, for example by a spray nozzle or revolving disc. The amount of liquid is typically determined by the assay of the formulation and the required rate of active ingredient necessary for efficacy. As the seed falls into the treatment equipment the seed can be treated (for example by misting or spraying with the seed treatment composition) and passed through the treater under continual movement/tumbling where it can be coated evenly and dried before storage or use.

In another embodiment, a known weight of seeds can be introduced into the treatment equipment (such as a tumbler, a mixer, or a pan granulator). A known volume of seed treatment composition can be introduced into the treatment equipment at a rate that allows the seed treatment composition to be applied evenly over the seeds. During the application, the seed can be mixed, for example by spinning or tumbling. The seed can optionally be dried or partially dried during the tumbling operation. After complete coating, the treated sample can be removed to an area for further drying or additional processing, use, or storage.

In still another embodiment, seeds can be coated in laboratory size commercial treatment equipment such as a tumbler, a mixer, or a pan granulator by introducing a known weight of seeds in the treater, adding the desired amount of seed treatment composition, tumbling or spinning the seed and placing it on a tray to thoroughly dry.

In another embodiment, seeds can also be coated by placing the known amount of seed into a narrow neck bottle or receptacle with a lid. While tumbling, the desired amount of seed treatment composition can be added to the receptacle. The seed is tumbled until it is coated with the seed treatment composition. After coating, the seed can optionally be dried, for example on a tray.

In yet another embodiment of the present invention, a pesticide can be introduced onto or into a seed by use of solid matrix priming. For example, a quantity of the pesticide can be mixed with a solid matrix material and then the seed can be placed into contact with the solid matrix material for a period to allow the pesticide to be introduced to the seed. The seed can then optionally be separated from the solid matrix material and stored or used, or the mixture of solid matrix material plus seed can be stored or planted directly. Solid matrix materials which are useful in the present invention include polyacrylamide, starch, clay, silica, alumina, soil, sand, polyurea, polyacrylate, or any other material capable of absorbing or adsorbing the pesticide for a time and releasing that pesticide into or onto the seed. It is useful to make sure that the pesticide and the solid matrix material are compatible with each other. For example, the solid matrix material should be chosen so that it can release the pesticide at a reasonable rate, for example over a period of minutes, hours, or days.

The present invention further embodies imbibition as another method of treating seed with the pesticide. For example, plant seed can be combined for a period of time with a solution comprising from about 1% by weight to about 75% by weight of the pesticide in a solvent such as water. Preferably the concentration of the solution is from about 5% by weight to about 50% by weight, more preferably from about 10% by weight to about 25% by weight. During the period that the seed is combined with the solution, the seed takes up (imbibes) a portion of the pesticide. Optionally, the mixture of plant seed and solution can be agitated, for example by shaking, rolling, tumbling, or other means. After imbibition, the seed can be separated from the solution and optionally dried, for example by patting or air drying.

In yet another embodiment, a powdered pesticide can be mixed directly with seed. Optionally, a sticking agent can be used to adhere the powder to the seed surface. For example, a quantity of seed can be mixed with a sticking agent and optionally agitated to encourage uniform coating of the seed with the sticking agent. The seed coated with the sticking agent can then be mixed with the powdered pesticide. The mixture can be agitated, for example by tumbling, to encourage contact of the sticking agent with the powdered pesticide, thereby causing the powdered pesticide to stick to the seed.

The present invention also provides a seed that has been treated by the method described above.

Another embodiment of the invention is a seed that is protected against multiple pests. In this embodiment, the seed has at least one heterologous gene encoding for the expression of a protein that is active against a first pest and, in addition, at least one pesticide in an amount effective to provide protection to the shoots and foliage of the plant against damage by at least one second pest. These treated transgenic seeds can be provided by the method described above, or by any other method.

The treated seeds of the present invention can be used for the propagation of plants in the same manner as conventional treated seed. The treated seeds can be stored, handled, sowed and tilled in the same manner as any other pesticide treated seed. Appropriate safety measures should be taken to limit contact of the treated seed with humans, food or feed materials, water and birds and wild or domestic animals.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples.

EXAMPLE 1

This example compares the efficacy of seed treatment with lambda-cyhalothrin (CAS# 91465-08-6) to soil granular treatments with tefluthrin (CAS # 79538-32-2) against feeding damage by black cutworm larvae on shoots and foliage.

A lambda-cyhalothrin seed treatment formulation was prepared by diluting the WARRIOR® T insecticide (Zeneca Ag Products, Wilmington, Del.), which contains 11.4% lambda-cyhalothrin as the active ingredient, into water as a carrier. This formulation was applied for one minute at room temperature to twenty-five grams of Pioneer corn seed (Cultivar PN3394) in a rotostatic seed treater at a rate of 125 g, 250 g or 500 g active ingredient (AI) to 100 kg seed The treated seeds were allowed to sit uncapped for four to twenty-four hours before planting.

Treated and untreated seeds (Pioneer hybrid PN3394) were planted in a soil mix consisting of Dupo silt loam, 30% Perlite, 20% coarse sand (WB-10 grade) in six groups of tubs (20 in. L×15 in. W×8 in. D). Twelve seeds were planted per tub and three tubs were planted for each treatment regimen. Soil applications of FORCE® 3GR, which contains 3% tefluthrin granule as the active ingredient, were used for two sets of tubs containing untreated seeds. The FORCE 3GR was applied either in-furrow or incorporated into a 5 inch band on the soil surface at the time of planting. The tubs were overhead irrigated until the plants were infested with black cutworm larvae.

The rate of application for the FORCE 3GR was reported in units of grams of the active ingredient per hectare (g/ha), while the rate of application of the WARRIOR T to the seeds was reported in units of grams of the active ingredient per 100 kilograms of the seeds (g/100 kg). Although the conversion of one of these units to the other will vary somewhat according to the type of seed that is being used, the size and weight of the seed, and the density of planting that is used—among other things—an approximate conversion for corn seed can be carried out as follows. Assuming a seed application rate of lambda cyhalothrin of, for example, 125 g/100 kg of seed and a planting density of 15 lbs seed/ac, about 14.7 acres can be planted with 100 kg of the seed. This is an effective application rate of about 8.5 g of lambda cyhalthrin per acre. At 2.47 ac/ha, the seed treatment level of 125 g/100 kg is approximately equivalent to a surface banding treatment at about 21 g/ha.

At twelve days after planting (DAP) but before infestation, the overall health of each plant was rated by looking at emergence, height and appearance. This vigor rating gives an indication of any phytotoxicity from the seed or soil treatment. A rating of 1 indicates extremely low vigor while 10 is the highest vigor rating.

The corn plants were infested at 12 DAP, which corresponds to late growth stage V1 by placing two black cutworm larvae at 3/4 instar on the soil surface near the base of the plant. Plants were rated 3, 7 and 10 days after infestation (DAI) for the number of cut plants, as well as damage from leaf feeding. The percent stand reduction due to plant cutting was calculated by dividing the number of cut plants into the number of plants present at infestation. The foliar feeding injury was evaluated using a rating scale of 1=no damage and 10=complete defoliation. The mean results for the three tubs for each treatment regimen are presented in Table 2 below.

TABLE 2

Efficacy of lambda-cyhalothrin seed-treatment against black cutworm feeding damage on corn.

| Treatment Regimen | Vigor at 12 DAP | % Stand Reduct'n 3 DAI | Plant Defol. 3 DAI | % Stand Reduct'n 7 DAI | Plant Defol. 7 DAI | % Stand Reduct'n 10 DAI | Plant Defol. 10 DAI |
|---|---|---|---|---|---|---|---|
| None | 8.0 | 72.8 | 9.0 | 94.4 | 9.3 | 100.0 | 10.0 |
| λ-cyhalothrin seed 125 g/100 kg | 9.0 | 13.9 | 4.3 | 16.7 | 5.0 | 19.4 | 3.3 |
| λ-cyhalothrin seed 250 g/100 kg | 8.3 | 3.0 | 3.7 | 3.0 | 2.7 | 3.0 | 1.7 |
| λ-cyhalothrin seed 500 g/100 kg | 8.3 | 0.0 | 2.0 | 0.0 | 2.3 | 0.0 | 1.0 |
| Tefluthrin in-furrow 30 g/ha | 9.0 | 33.9 | 5.0 | 48.0 | 6.0 | 48.0 | 5.3 |
| Tefluthrin banded 30 g/ha | 8.7 | 0.0 | 1.7 | 0.0 | 1.7 | 0.0 | 0.3 |

These results demonstrate that seed treatment with lambda-cyhalothrin prior to planting provides significant protection of corn plants against shoot/foliar feeding damage by black cutworm. For example, at 7 DAI with the lowest rate tested (125 g/kg seed), a significant reduction was observed for both plant cutting (16.7% for seed treatment vs. 94% for untreated control) and foliar feeding injury (5.0 for seed treatment vs. 9.3 rating for untreated control) In addition, tubs planted with seed treated with lambda-cyhalothrin at rates of 250 and 500 g/100 kg seed, showed essentially no stand reduction from plant cutting (3% and 0% for 250 and 500 g, respectively) and only low levels of foliar injury (2.7 and 2.3 rating for 250 and 500 g, respectively). This level of protection was equal to the tefluthrin soil band treatment and superior to tefluthrin in-furrow treatment. When the tubs were evaluated at 10 DAI, no increase in plant cutting and only slightly higher ratings for foliar feeding injury were observed with lambda-cyhalothrin seed treatments as compared to evaluations at 7 DAI. In contrast, the untreated control tubs exhibited 100% plant cutting and complete defoliation by 10 DAI.

EXAMPLE 2

This example illustrated the efficacy of corn seed treatment by tefluthrin (CAS # 79538-32-2) and lambda cyhalothrin (CAS#91465-08-6) for protection of shoots and foliage against damage by black cutworms.

A lambda-cyhalothrin seed treatment formulation was prepared from the WARRIOR T insecticide and corn seed was prepared and treated as described in Example 1, except that the treatment levels were 88, 185 and 381 gm active ingredient/100 kg seed. Treated and untreated seeds were planted and cultivated as described in Example 1. Again, FORCE 3GR was applied either in-furrow or incorporated into a 5 inch band on the soil surface at the time of planting. The tubs were overhead irrigated until the plants were infested with black cutworm larvae.

The corn plants were infested at 12 DAP, as described in Example 1. Plants were rated at 10 days after infestation (DAI) for the number of cut plants. The percent stand reduction due to plant cutting was calculated by dividing the number of cut plants into the number of plants present at infestation. The mean results for the three tubs for each treatment regimen are presented in Table 3, below.

as did the use of FORCE 3GR in a 5" surface band at 30 gm AI/ha.

The advantage of the seed treatment over either in-furrow or banded treatment is the increased simplicity during planting and the decreased environmental distribution of the pesticide. No applications other than planting the seed are required during sowing and the pesticide, because it is totally buried in the soil with the seed, is not exposed to the surface of the soil for access by birds, animals, rain or beneficial insects.

TABLE 3

Comparison of the efficacy of seed treatment of corn by lambda cyhalothrin (CAS # 91645-08-6) at different levels with standard in-furrow and band application against stand reduction by black cutworm larvae.

| TREATMENT | FORM OF INSECTICIDE | APPLICATION RATE (gm Active Ingredient/100 kg of seed) | TYPE OF TREATMENT | STAND REDUCTION (%, 10 days after infestation) |
|---|---|---|---|---|
| UNTREATED CHECK | n/a | 0 | no treatment | 100 |
| WARRIOR T[a] | 11.4 CS | 88 | seed treatment | 19.44 |
| WARRIOR T | 11.4 CS | 185 | seed treatment | 3.03 |
| WARRIOR T | 11.4 CS | 381 | seed treatment | 0 |
| FORCE[b] | 3 GR | 30 gm/ha | in furrow[d] | 47.98 |
| FORCE | 3 GR | 30 gm/ha | 5" banded[d] | 0 |
| LSD (0.05)[c] | | | | 35.99 |

Notes:
[a]WARRIOR T 11.4 CS is a capsule suspension (CS) containing 11.4% lambda cyhalothrin and is available from Zeneca Ag Products, Wilmington, DE.
[b]FORCE is a granular (3 GR) form containing 3% tefluthrin that is available from Zeneca Ag Products, Wilmington, DE.
[c]LSD (0.05) represents the number of percentage points of difference that are required to indicate a level of significant difference at a confidence level of 95%.
[d]In-furrow and banded treatments with FORCE 3 GR were carried out by simulating conventional agricultural practice. In-furrow treatment was carried out by depositing the granules in the furrow along with the seed. In the banded treatment, a 5"-wide band of the granules was laid down over the closed furrow and incorporated into the top 1" of soil.

d. In-furrow and banded treatments with FORCE 3GR were carried out by simulating conventional agricultural practice. In-furrow treatment was carried out by depositing the granules in the furrow along with the seed. In the banded treatment, a 5"-wide band of the granules was laid down over the closed furrow and incorporated into the top 1" of soil.

The results of the test show that seed treatment with lambda cyhalothrin at all levels gave significant protection to post emergent corn against cutworm damage to shoots and foliage. For example, at the lowest level tested (88 g AI/100 kg seed), only 19.4% of the plants sustained damage compared with 100% of the untreated plants. At higher levels (185 and 381 gm AI/100 kg seed), the damage was essentially reduced to zero or near zero. All levels of seed treatment provided better protection than in-furrow treatment with FORCE 3GR. Seed treatment at 381 gm AI/100 kg seed provided total protection,

EXAMPLE 3

This example illustrates the efficacy of corn seed treatment with cyfluthrin (CAS#68359-37-5) for the protection of post-emergent corn from damage by black cutworms.

A cyfluthrin seed treatment formulation was prepared from the BAYTHROID 25 EC formulation of cyfluthrin (Bayer Chemical Co.) and corn seed was prepared and treated as described in Example 1, except that the treatment levels were 168, 393 and 702 gm active ingredient/100 kg seed. Treated and untreated seeds were planted and cultivated as described in Example 1. The tubs were overhead irrigated until the plants were infested with black cutworm larvae.

The corn plants were infested at 12 DAP, as described in Example 1. Plants were rated at 10 days after infestation (DAI) for the number of cut plants. The percent stand reduction due to plant cutting was calculated by dividing the number of cut plants into the number of plants present at infestation. The mean results for the three tubs for each treatment regimen are presented in Table 4, below.

TABLE 4

The efficacy of seed treatment of corn by cyfluthrin (CAS # 68359-37-5) at different levels against stand reduction by black cutworm larvae.

| TREATMENT | FORM OF INSECTICIDE | APPLICATION RATE (gm Active Ingredient/100 kg of seed) | TYPE OF TREATMENT | STAND REDUCTION (%, 10 days after infestation) |
|---|---|---|---|---|
| UNTREATED CHECK | n/a | 0 | no treatment | 100 |
| BAYTHROID[a] | 25 EC | 168 | seed treatment | 65.9 |
| BAYTHROID | 25 EC | 393 | seed treatment | 54.8 |

TABLE 4-continued

The efficacy of seed treatment of corn by cyfluthrin (CAS # 68359-37-5) at different levels against stand reduction by black cutworm larvae.

| TREATMENT | FORM OF INSECTICIDE | APPLICATION RATE (gm Active Ingredient/100 kg of seed) | TYPE OF TREATMENT | STAND REDUCTION (%, 10 days after infestation) |
|---|---|---|---|---|
| BAYTHROID | 25 EC | 702 | seed treatment | 38.7 |
| LSD (0.05)[b] | | | | 30.64 |

Notes:
[a]BAYTHROID 25 EC is an emulsifiable concentrate (EC) form of cyfluthrin containing 25% active ingredient and is available from Bayer.
[b]LSD (0.05) represents the number of percentage points of difference that are required to indicate a level of significant difference at a confidence level of 95%.

The results of the test showed that seed treatment with cyfluthrin at any level tested provided significant protection to corn shoots and foliage from damage by cutworm larvae compared with untreated seed. The level of protection that was provided increased as the treatment level increased, but the difference in protection between the highest and lowest treatment level was not significant.

EXAMPLE 4

This example illustrates the protection of post-emergent corn plants from damage by black cutworms by seed treatment with lambda cyhalothrin or banded treatment with tefluthrin when the seeds were planted in three different soil types.

A lambda-cyhalothrin seed treatment formulation was prepared from WARRIOR T insecticide and corn seed was prepared and treated as described in Example 1, except that the treatment level was 250 gm active ingredient/100 kg seed. Treated and untreated seeds were planted and cultivated as described in Example 1. FORCE 3GR was applied and incorporated into a 5 inch band on the soil surface at the time of planting. The untreated seed—with and without tefluthrin banding—and the treated seed were planted in three different soil types. Soil type I was Dupo silt loam (having 9% sand, 78% silt and 13% clay and having an organic matter content of 1.1%); soil type II was Muscatine silt loam (having 25% sand, 57% silt and 18% clay and having an organic matter content of 2.5%); and soil type III was as described in Example 1. The tubs were overhead irrigated until the plants were infested with black cutworm larvae.

The corn plants were infested at 12 DAP, as described in Example 1. Plants were rated at 10 days after infestation (DAI) for the number of cut plants. The percent stand reduction due to plant cutting was calculated by dividing the number of cut plants into the number of plants present at infestation. The mean results for the three tubs for each treatment regimen are presented in Table 5, below.

TABLE 5

Comparison of the efficacy of seed treatment of corn by lambda cyhalothrin with untreated seed with and without tefluthrin band treatment in three different soil types against stand reduction by black cutworm larvae.

| TREATMENT | FORM OF INSECTICIDE | APPLICATION RATE (gm Active Ingredient/100 kg of seed) | TYPE OF TREATMENT | STAND REDUCTION (%, 10 days after infestation) |
|---|---|---|---|---|
| SOIL TYPE I | | | | |
| UNTREATED CHECK | n/a | 0 | no treatment | 100 |
| WARRIOR T[a] | 11.4 CS | 250 | seed treatment | 80.56 |
| FORCE[b] | 3 GR | 30 | 5" banded[d] | 0 |
| SOIL TYPE II | | | | |
| UNTREATED CHECK | | 0 | no treatment | 100 |
| WARRIOR T | 11.4 CS | 250 | seed treatment | 39.8 |
| FORCE | 3 GR | 30 | 5" banded | 0 |
| SOIL TYPE III | | | | |
| UNTREATED CHECK | | 0 | no treatment | 100 |
| WARRIOR T | 11.4 CS | 250 | seed treatment | 72.4 |
| FORCE | 3 GR | 30 | 5" banded | 0 |
| LSD (0.05)[c] | | | | 33.9 |

Notes:
[a]WARRIOR T 11.4 CS is a capsule suspension (CS) containing 11.4% lambda cyhalothrin and is available from Zeneca Ag Products, Wilmington, DE.
[b]FORCE 3 GR is a granular (GR) form containing 3% tefluthrin that is available from Zeneca Ag Products, Wilmington, DE.
[c]LSD (0.05) represents the number of percentage points of difference that are required to indicate a level of significant difference at a confidence level of 95%.
[d]Banded treatment with FORCE 3 GR was carried out according to simulated conventional agricultural practice - a 5"-wide band of the granules was laid down over the closed furrow and incorporated into the top 1" of soil.

The results of the test showed that the type of soil had a significant effect upon the efficacy of seed treatment with lambda cyhalothrin, but no effect upon the efficacy of the band treatment using tefluthrin. Although the seed treatment with lambda cyhalothrin at 250 gm AI/100 kg seed provided improved protection in all soil types, the protection was significant only in Soil Type II. The banded treatment with tefluthrin provided total protection in all soil types, but seed treatment in Soil Type I was not significant at 80.1%, or in Soil Type III at 72.4%. Protection in Soil Type II at 39.8% was significant, but not as complete as banded treatment with tefluthrin. No reason for the effect of the soil type upon the degree of protection provided by the seed treatment was evident.

EXAMPLE 5

This example illustrates the efficacy of corn seed treatment with lambda cyhalothrin and tefluthrin for the protection of post emergent corn against damage by black cutworm.

A lambda-cyhalothrin seed treatment formulation was prepared from the WARRIOR T insecticide and corn seed was prepared and treated as described in Example 1, except that the treatment levels were 125, 228 and 358 gm active ingredient/100 kg seed. A tefluthrin seed treatment formulation was also prepared from RAZE 2.5 FS, which contains tefluthrin as the active ingredient, into water as a carrier. Treated and untreated seeds were planted and cultivated as described in Example 1. Again, FORCE 3GR was applied and incorporated into a 5 inch band on the soil surface at the time of planting. The tubs were overhead irrigated until the plants were infested with black cutworm larvae.

The corn plants were infested at 12 DAP, as described in Example 1. Plants were rated at 10 days after infestation (DAI) for the number of cut plants. The percent stand reduction due to plant cutting was calculated by dividing the number of cut plants into the number of plants present at infestation. The mean results for the three tubs for each treatment regimen are presented in Table 6, below.

The results of the test showed that seed treatment by lambda cyhalothrin provided significant protection against black cutworm damage at treatment levels at and above 228 gm AI/100 kg seed. Below that level, the damage level was reduced over that for the untreated seed, but the level of reduction was not significant. Seed treated with tefluthrin from RAZE 2.5 FS showed increased protection over untreated seed at all levels of treatment, but not level of treatment provided improvement that was statistically significant. Neither seed treatment equaled the protection provided by banded treatment with tefluthrin, which provided total protection.

EXAMPLE 6

This example illustrates the efficacy of corn seed treatment with permethrin (CAS#52645-53-1) for the protection of post-emergent corn from damage by black cutworms.

A permethrin seed treatment formulation was prepared from the ASSAULT 25 WP formulation of permethrin (Zeneca Ag Products) and corn seed was prepared and treated as described in Example 1, except that the treatment levels were 202, 411 and 583 gm active ingredient/100 kg seed. Treated and untreated seeds were planted and cultivated as described in Example 1. Again, FORCE 3GR was applied and incorporated into a 5 inch band on the soil surface at the time of planting. The tubs were overhead irrigated until the plants were infested with black cutworm larvae.

The corn plants were infested at 12 DAP, as described in Example 1. Plants were rated at 10 days after infestation (DAI) for the number of cut plants. The percent stand reduction due to plant cutting was calculated by dividing the number of cut plants into the number of plants present at infestation. The mean results for the three tubs for each treatment regimen are presented in Table 7, below.

TABLE 6

Comparison of the efficacy of seed treatment of corn by lambda cyhalothrin (CAS # 91645-08-6) or tefluthrin at different levels with standard band application against stand reduction by black cutworm larvae

| TREATMENT | FORM OF INSECTICIDE | APPLICATION RATE (gm Active Ingredient/100 kg of seed) | TYPE OF TREATMENT | STAND REDUCTION (%, 10 days after infestation) |
|---|---|---|---|---|
| UNTREATED CHECK | n/a | 0 | no treatment | 100 |
| WARRIOR T[a] | 11.4 CS | 125 | seed treatment | 85.6 |
| WARRIOR T | 11.4 CS | 228 | seed treatment | 64.4 |
| WARRIOR T | 11.4 CS | 358 | seed treatment | 69.5 |
| RAZE[b] | 2.5 FS | 137 | seed treatment | 80.6 |
| RAZE | 2.5 FS | 287 | seed treatment | 84.2 |
| RAZE | 2.5 FS | 461 | seed treatment | 78.1 |
| RAZE | 2.5 FS | 613 | seed treatment | 88.4 |
| FORCE[c] | 3 GR | 30 (grams/hectare) | band w/incorporation[e] | 0 |
| LSD (0.05)[d] | | | | 24.6 |

Notes:
[a]WARRIOR T 11.4 CS is a capsule suspension (CS) containing 11.4% lambda cyhalothrin and is available from Zeneca Ag Products, Wilmington, DE.
[b]RAZE 2.5 FS is a flowable solid (FS) preparation containing 26.8% active tefluthrin that is labeled for use for treatment of corn seed and the protection of corn seed against damage by wireworm. It is available from the Wilbur-Ellis Company.
[c]FORCE 3 GR is a granular (GR) form containing 3% tefluthrin that is available from Zeneca Ag Products, Wilmington, DE.
[d]LSD (0.05) represents the number of percentage points of difference that are required to indicate a level of significant difference at a confidence level of 95%.
[e]Banded treatment with FORCE 3 GR was carried out according to simulated conventional agricultural practice - a 5"-wide band of the granules was laid down over the closed furrow and incorporated into the top 1" of soil.

TABLE 7

The efficacy of seed treatment of corn by permethrin (CAS # 52645-53-1) at different levels against stand reduction by black cutworm larvae.

| TREATMENT | FORM OF INSECTICIDE | APPLICATION RATE (gm Active Ingredient/100 kg of seed) | TYPE OF TREATMENT | STAND REDUCTION (%, 10 days after infestation) |
|---|---|---|---|---|
| UNTREATED CHECK | n/a | 0 | no treatment | 94.45 |
| ASSAULT[a] | 25 WP | 202 | seed treatment | 88.9 |
| ASSAULT | 25 WP | 411 | seed treatment | 77.8 |
| ASSAULT | 25 WP | 583 | seed treatment | 66.7 |
| FORCE[b] | 3 GR | 30 (grams/hectare) | band w/ incorporation[d] | 0 |
| LSD (0.05)[c] | | | | 19.3 |

Notes:
[a]ASSAULT 25 WP is a wettable powder (WP) preparation of permethrin available from Gustfson. It contains 25% active ingredient.
[b]FORCE 3 GR is a granular (GR) form containing 3% tefluthrin that is available from Zeneca Ag Products, Wilmington, DE.
[c]LSD (0.05) represents the number of percentage points of difference that are required to indicate a level of significant difference at a confidence level of 95%.
dBanded treatment with FORCE 3 GR was carried out according to simulated conventional agricultural practice - a 5"-wide band of the granules was laid down over the closed furrow and incorporated into the top 1" of soil.

The results of the test showed that seed treatment with permethrin at all levels gave some protection to corn, and the protection was significant at all levels above 411 gm AI/100 kg seed. No level of seed treatment provided the same protection as the banded treatment with tefluthrin. The degree of protection provided by seed treatment with permethrin increased with increasing dosage level.

EXAMPLE 7

This example illustrates the protection of post-emergent corn from damage by black cutworm by treatment of corn seed with bifenthrin (CAS#82657-04-3), lambda cyhalothrin (CAS#91465-08-6) and tefluthrin (CAS#79538-32-2).

A lambda-cyhalothrin seed treatment formulation was prepared from WARRIOR T 11.4 CS formulation (Zeneca Ag Products, Wilmington, Del.), as described in Example 1. A seed treatment formulation was also prepared by the method as described in Example 1, except from CAPTURE® 2 EC (bifenthrin; available from FMC). Also, a seed treatment formulation was prepared from RAZE 2.5 FS formulation (available from Wilbur-Ellis Co.), containing 26.8% tefluthrin. Each of these seed treatment formulations were applied for one minute at room temperature to twenty-five grams of Pioneer corn seed (Cultivar PN3394) in a rotostatic seed treater at the treatment rates noted in Table 8, below. The treated seeds were allowed to sit uncapped for four to twenty-four hours before planting.

Treated and untreated seeds (Pioneer hybrid PN3394) were planted in a soil mix consisting of Dupo silt loam, 30% Perlite, 20% coarse sand (WB-10 grade) in six groups of tubs (20 in. L×15 in. W×8 in. D). Twelve seeds were planted per tub and three tubs were planted for each treatment regimen. Soil applications of FORCE 3 GR, which contains 3% tefluthrin granule as the active ingredient, were used for two sets of tubs containing untreated seeds. The FORCE 3 GR was applied and incorporated into a 5 inch band on the soil surface at the time of planting. The tubs were overhead irrigated until the plants were infested with black cutworm larvae.

The corn plants were infested at 12 DAP, which corresponds to late growth stage 11 by placing two black cutworm larvae at 3/4 instar on the soil surface near the base of the plant. Plants were rated 10 days after infestation (DAI) for the number of cut plants. The percent stand reduction due to plant cutting was calculated by dividing the number of cut plants into the number of plants present at infestation. The mean results for the three tubs for each treatment regimen are presented in Table 8, below.

TABLE 8

Efficacy of bifenthrin, lambda-cyhalothrin and tefluthrin seed-treatment against black cutworm feeding damage on corn.

| TREATMENT | FORM OF INSECTICIDE | APPLICATION RATE (gm Active Ingredient/100 kg of seed) | TYPE OF TREATMENT | STAND REDUCTION (%, 10 days after infestation) |
|---|---|---|---|---|
| UNTREATED CHECK | n/a | 0 | no treatment | 59.9 |
| CAPTURE[a] | 2 EC | 209 | seed treatment | 0 |
| CAPTURE | 2 EC | 417 | seed treatment | 5.6 |
| CAPTURE | 2 EC | 416 | seed treatment | 11.1 |
| WARRIOR T[b] | 11.4 CS | 535 | seed treatment | 25.2 |
| WARRIOR T | 11.4 CS | 681 | seed treatment | 35.1 |
| RAZE[c] | 2.5 FS | 483 | seed treatment | 61.9 |
| RAZE | 2.5 FS | 675 | seed treatment | 50 |

TABLE 8-continued

Efficacy of bifenthrin, lambda-cyhalothrin and tefluthrin seed-treatment against black cutworm feeding damage on corn.

| TREATMENT | FORM OF INSECTICIDE | APPLICATION RATE (gm Active Ingredient/100 kg of seed) | TYPE OF TREATMENT | STAND REDUCTION (%, 10 days after infestation) |
|---|---|---|---|---|
| FORCE[d] | 3 GR | 30 (grams/hectare) | band w/incorporation[f] | 5.6 |
| LSD (0.05)[e] | | | | 15.4 |

Notes:
[a]CAPTURE 2 EC is an emulsifiable concentrate (EC) containing 25.1% bifenthrin and is available from FMC Corporation, Princeton, NJ.
[b]WARRIOR T 11.4 CS is a capsule suspension (CS) containing 11.4% lambda cyhalothrin and is available from Zeneca Ag Products, Wilmington, DE.
[c]RAZE 2.5 FS is a flowable solid (FS) preparation containg 26.8% active tefluthrin that is labled for use for treatment of corn seed and the protection of corn seed against damage by wireworm. It is available from the Wilbur-Ellis Company.
[d]FORCE 3 GR is a granular (GR) form containing 3% tefluthrin that is available from Zeneca Ag Products, Wilmington, DE.
[e]LSD (0.05) represents the number of percentage points of difference that are required to indicate a level of significant difference at a confidence level of 95%.
[f]Banded treatment with FORCE 3 GR was carried out according to simulated conventional agricultural practice - a 5"-wide band of the granules was laid down over the closed furrow and incorporated into the top 1" of soil.

The results of the test showed that the bifenthrin and lambda cyhalothrin seed treatments provided significant protection at all levels tested. In fact, treatment of seed with befenthrin at 209 gm AI/100 kg seed provided total protection of the seed, which was better than the protection provided by banded treatment with tefluthrin. Lambda cyhalothrin provided significant protection at all levels tested, but the degree of protection was not as high as that provided by seed treatment with bifenthrin or by banded treatment with tefluthrin. Seed treatment with tefluthrin did not seem to provide any improvement over the untreated seeds. It was noted, however, that the degree of damage to untreated seed in this test was only about 60%, which was lower than the level of damage of untreated seed in other examples.

EXAMPLE 8

This example illustrates the efficacy of corn seed treatment with tefluthrin compared with lambda cyhalothrin for protection of corn shoots and foliage against damage by black cutworm larvae.

A lambda-cyhalothrin seed treatment formulation was prepared from WARRIOR T 11.4 CS formulation (Zeneca Ag Products, Wilmington, Del.), as described in Example 1. Also, a tefluthrin seed treatment formulation was prepared from RAZE 26.8 FS formulation (available from Wilbur-Ellis Co.), by the same method. Each of these seed treatment formulations were applied for one minute at room temperature to twenty-five grams of Pioneer corn seed (Cultivar PN3394) in a rotostatic seed treater at the treatment rates noted in Table 9, below. The treated seeds were allowed to sit uncapped for four to twenty-four hours before planting.

Treated and untreated seeds (Pioneer hybrid PN3394) were planted in a soil mix consisting of Dupo silt loam, 30% Perlite, 20% coarse sand (WB-10 grade) in six groups of tubs (20 in. L×15 in. W×8 in. D). Twelve seeds were planted per tub and three tubs were planted for each treatment regimen. Soil applications of FORCE 3GR, which contains 3% tefluthrin as the active ingredient, were used for two sets of tubs containing untreated seeds. The FORCE 3GR was applied and incorporated into a 5 inch band on the soil surface at the time of planting. The tubs were overhead irrigated until the plants were infested with black cutworm larvae.

The corn plants were infested at 12 DAP, which corresponds to late growth stage 11 by placing two black cutworm larvae at 3/4 instar on the soil surface near the base of the plant. Plants were rated 10 days after infestation (DAI) for the number of cut plants. The percent stand reduction due to plant cutting was calculated by dividing the number of cut plants into the number of plants present at infestation. The mean results for the three tubs for each treatment regimen are presented in Table 9, below.

TABLE 9

Efficacy of tefluthrin formulation from RAZE 26.8 FS compared with lambda cyhalothrin formulation from WARRIOR T 11.4 CS seed-treatment against black cutworm feeding damage on corn.

| TREATMENT | FORM OF INSECTICIDE | APPLICATION RATE (gm Active Ingredient/100 kg of seed) | TYPE OF TREATMENT | STAND REDUCTION (%, 10 days after infestation) |
|---|---|---|---|---|
| UNTREATED CHECK | n/a | 0 | no treatment | 52.8 |
| RAZE[a] | 26.8 FS | 450 | seed treatment | 39.1 |
| RAZE | 26.8 FS | 750 | seed treatment | 59.8 |
| WARRIOR T[b] | 11.4 CS | 404 | seed treatment | 27.3 |
| FORCE | 3 GR | 30 (grams/hectare) | band w/incorporation[d] | 0 |
| LSD (0.05)[c] | | | | 23.9 |

Notes:
[a]RAZE is a flowable solid (FS) preparation containg 26.8% active tefluthrin that is labled for use for treatment of corn seed and the protection of corn seed against damage by wireworm. It is available from the Wilbur-Ellis Company.
[b]WARRIOR T 11.4 CS is a capsule suspension (CS) containing 11.4% lambda cyhalothrin and is available from Zeneca Ag Products, Wilmington, DE.
[c]LSD (0.05) represents the number of percentage points of difference that are required to indicate a level of significant difference at a confidence level of 95%.
[d]Banded treatment with FORCE 3 GR was carried out according to simulated conventional agricultural practice - a 5"-wide band of the granules was laid down over the closed furrow and incorporated into the top 1" of soil.

The results of the test showed that the tefluthrin seed treatment from the lambda cyhalothrin formulation provide significant protection for the corn from damage by cutworms. The seed treated with the RAZE formulation of tefluthrin showed no significant protection. The banded treatment with tefluthrin provided total protection.

EXAMPLE 9

This example illustrates the protection of corn from damage by black cutworm in field trials at three different sites in the Midwest.

Corn seed, (ASGROW RX 601) was treated as described in Example 1 with either WARRIOR® T (11.4% by weight lambda cyhalothrin; available from Zenneca Ag Products, Wilmington, Del.); or RAZE® (26.8% tefluthrin; available from Wilbur-Ellis Co.) at the rates of application noted in Table 10. The treated corn seed was planted at three different field sites in the Midwest by standard sowing methods along with an untreated check sample of the same seed. In addition, untreated seed also received an 8" band of either FORCE® 3G granules or LORSBAN® 15G granules (chlorpyrifos; available from Dow-Elanco). The last two treatments are commercial standard at-planting soil granule treatments for broad spectrum soil insect control on corn. Forty (40) seed were planted per plot and there were 4 replicate plots per treatment. Corn plants were infested with 4th instar black cutworm larvae at crop stage V2. Plant cutting by black cutworm was evaluated for 14 days after infestation.

TABLE 10

Damage by black cutworms to emergent corn having no treatment; seed treatment by tefluthrin or lambda cyhalothrin at different levels; or by standard band treatment at sowing with LORSBAN or FORCE in granular form at three field sites in the Midwest.

| TREATMENT | APPLICATION RATE (gm Active Ingredient/ 100 kg seed) | SITE I (% cut plants) | SITE II (% cut plants) | SITE III (% cut plants) |
|---|---|---|---|---|
| UNTREATED CHECK | 0 | 78 | 49.3 | 17.4 (52)[a] |
| WARRIOR T | 250 | 19 | 49.9 | 8.7 |
| WARRIOR T | 500 | 14 | 37.8 | 15.6 |
| WARRIOR T | Average[b] | 17 | 44 | 12 |
| RAZE | 500 | 15 | 57 | 17 |
| LORSBAN | 0.112[c] | 29 | 31.2 | 11.1 |
| FORCE 3 GR | 0.011[c] | 44 | 17.4 | 2.8 |
| LSD (0.05)[d] | | 25 | 23 | ns |

Notes:
[a] Injury level in one rep was 52%; injury levels in other reps was close to 0.
[b] The average degree of damage was calculated as the average for all levels of insecticide seed treatment.
[c] LORSBAN and FORCE 3 GR were applied according to label instructions as 8"-wide bands of granules broadcast and incorporated over the seed furrow. The application rates are expressed as grams of active ingredient per meter of row length.
[d] LSD (0.05) represents the number of percentage points of difference that are required to indicate a level of significant difference at a confidence level of 95%.

The results from this example show that the level of damage on the untreated check plants varied among the three sites from a high of 78% at Site I to a low of 17% at Site III. However, in the Site III test, damage to plants in different repetitions varied from substantially zero, up to 52%. Moreover, it was found that the efficacy of the seed treatment with pyrethroids varied among the three sites compared with the conventional banded treatment with LORSBAN or FORCE.

At Site I, seed treatment with lambda cyhaothrin from WARRIOR at 250 and 500 gm/100 kg seed, provided significant protection to plant shoots and foliage from damage by cutworms. Damage at these two treatment levels was 19% and 14%, respectively, and both levels of seed treatment provided better protection than FORCE 3GR applied as a band (damage level of 44%), and LORSBAN applied as a band (29% damage). Seed treatment with tefluthrin from RAZE at 500 gm/100 kg seed was inferior to protection provided by lambda cyhalothrin from WARRIOR T, but superior to protection provided by LORSBAN banded and significantly better than FORCE 3GR banded treatment.

The data show that seed treatment with synthetic pyrethroids at 0.25% and 0.5% by weight of seeds provided protection against damage to plant shoots and foliage that was equal to or better than that provided by conventional band treatment under certain field conditions.

At Site II, only FORCE 3 GR applied as a band at sowing provided significant protection against damage to plant shoots and foliage by cutworms. Lambda cyhalothrin from WARRIOR T provided a small degree of protection at the higher level of treatment, while RAZE provided no apparent protection as a seed treatment. LORSBAN applied in a band resulted in slightly better protection than the lambda cyhalothrin seed treatment at the higher level, and only FORCE 3 GR applied as a band resulted in significant protection (17% damage).

At Site III, due to the low level of damage in untreated plants, little difference could be seen among the various seed treatments and the standard banded treatments. As a general matter, however, all treatments seemed to result in some degree of protection. The lowest amount of damage occurred to the plants having FORCE 3 GR banded treatment, but such protection was not substantially different from the protection provided by the seed treatment or by LORSBAN.

In view of the above, it will be seen that the several advantages of the invention are achieved and other advantageous results attained.

As various changes could be made in the above methods and compositions without departing from the scope of the invention, it is intended that all matter contained in the above description and shown in the accompanying drawings shall be interpreted as illustrative and not in a limiting sense.

All references cited in this specification, including patents, patent applications, brochures, specification sheets, texts, periodicals, manuscripts, journals, internet web-page citations, and any other publications are hereby incorporated by reference. The discussion of references herein is intended merely to summarize the assertions made by their authors and no admission is made that any reference constitutes prior art. Applicants reserve the right to challenge the accuracy and pertinency of the cited references.

What is claimed is:

1. A method of preventing damage by a pest to shoots and foliage of a plant grown from a seed having an exogenous gene that encodes for the production of a protein having activity against European corn borer or corn root worm, the method comprising treating the seed with a composition comprising at least one insecticide selected from the group consisting of pyrethrin or synthetic pyrethroid that is selected on the basis of having an activity against an insect other than European corn borer or corn root worm.

2. The method as set forth in claim 1, wherein the insecticide is pyrethrin.

3. The method as set forth in claim 1, wherein the insecticide is a synthetic pyrethroid.

4. The method as set forth in claim 3, wherein the synthetic pyrethroid is selected from the group consisting of (s)-cyano (3-phenoxyphenyl)methyl 4-chloro alpha (1-methylethyl) benzeneacetate (fenvalerate), (S)-cyano (3-phenoxyphenyl) methyl (S)-4-chloro-alpha-(1-methylethyl)benzeneacetate (esfenvalerate), (3-phenoxyphenyl)-methyl(+)cis-trans-3-(2, 2-dichoroethenyl)-2,2-dimethylcyclopropanecarboxylate (permethrin), (±) alpha-cyano-(3-phenoxyphenyl)methyl(+)-cis,trans-3-(2,2-dichloroethenyl)-2,2-dimethyl-cyclopropane carboxylate (cypermethrin), theta cypermethrin, beta-cypermethrin, S-cyano (3-phenoxyphenyl)methyl (±) cis/trans 3-(2,2-dichloroethenyl) 2,2 dimethylcyclopropane carboxylate (zeta-cypermethrin), (s)-alpha-cyano-3-phenoxybenzyl (IR,3R)-3-(2,2-dibromovinyl)-2,2-dimethyl cyclopropanecarboxylate (deltamethrin), alpha-cyano-3-phenoxybenzyl 2,2,3,3,-tetramethyl cyclopropoanecarboxylate (fenpropathrin), (RS)-alpha-cyano-3-phenoxybenzyl (R)-2-[2-chloro-4-(trifluoromethyl)anilino]-3-methylbutanoate (tau-fluvalinate), (2,3,5,6-tetrafluoro-4-methylphenyl)-methyl-(1 alpha,3 alpha)-(Z)-(±)-3-(2-chloro-3,3,3-trifluoro-1-propenyl)-2,2-dimethylcyclopropanecarboxylate (tefluthrin), (±)-cyano (3-phenoxyphenyl)methyl (±)-4-(difluoromethoxy)-alpha-(1-methyl ethyl)benzeneacetate (flucythrinate), cyano(4-fluoro-3-phenoxyphenyl)methyl 3-[2-chloro-2-(4-chlorophenyl)ethenyl]-2,2-dimethylcyclopropanecarboxylate (flumethrin), cyano(4-fluoro-3-phenoxyphenyl)methyl 3-(2,2-dichloroethenyl)-2,2-dimethyl-cyclopropanedarboxylate (cyfluthrin), beta cyfluthrin, transfluthrin, (S)-alpha-cyano-3-phenoxybenzyl(Z)-(IR-cis)-2,2-dimethyl-3-[2-(2,2,2-trifluoro-trifluoromethyl-ethoxycarbonyl)vinyl]cyclopropane carboxylate (acrinathrin), (IR cis) S and (IS cis) R enantiomer isomer pair of alpha-cyano-3-phenoxybenzyl-3-(2,2dichlorovinyl)-2,2-dimethylcyclopropane carboxylate (alphacypermethrin), [IR,3S)3(1'RS)(1',2',2',2'-tetrabromoethyl)]-2,2-dimethyl cyclopropanecarboxylic acid (s)-alpha-cyano-3-phenoxybenzyl ester (tralomethrin), cyano-(3-phenoxyphenyl)methyl 2,2-dichloro-1-(4-ethoxyphenyl) cyclopropane carboxylate (cycloprothrin), [1α,3α(Z)]-(±)-cyano-(3-phenoxyphenyl)methyl 3-(2-chloro-3,3,3-trifluoro-1-propenyl)-2,2-cimethylcyclopropanecarboxylate (cyhalothrin), [1 alpha (s),3 alpha(z)]-cyano(3-phenoxyphenyl)methyl-3-(2-chloro-3,3,3-trifluoro-1-propenyl)-2,2-dimethylcyclopropane carboxylate (lambda cyhalothrin), (2-methyl [1,1'-biphenyl]-3-yl)methyl 3-(2-chloro-3,3,3-trifluoro-1-propenyl)-2,2-dimethyl-cyclopropanecarboxylate (bifenthrin), 5-1-benzyl-3-furylmethyl-d-cis(1R,3S,E)2,2-dimethyl-3-(2-oxo,-2,2,4,5 tetrahydro thiophenylidenemethyl)cyclopropane carboxylate (kadethrin, RU 15525), [5-(phenyl methyl)-3-furanyl]-3-furanyl 2,2-dimethyl-3-(2-methyl-1-propenyl)cyclopropane carboxylate (resmethrin), (1R-trans)-[5-(phenylmethyl)-3-furanyl]methyl 2,2-dimethyl-3-(2-methyl-1-propenyl)cyclopropanecarboxylate (bioresmethrin), 3,4,5,6-tetrahydro-phthalimidomethyl-(IRS)-cis-trans-chrysanthemate (tetramethrin), 3-phenoxybenzyl-d,l-cis,trans 2,2-dimethyl-3-(2-methylpropenyl)cyclopropane carboxylate (phenothrin), empenthrin, cyphenothrin, prallethrin, imiprothrin, (RS)-3-allyl-2-methyl-4-oxcyclopent-2-enyl-(1A,3R;1R,3S)-2,2-dimethyl-3-(2-methylprop-1-enyl)cyclopropane carboxylate (allethrin), bioallethrin, ZXI8901, and mixtures thereof.

5. The method as set forth in claim 3, wherein the synthetic pyrethroid is tefluthrin.

6. The method as set forth in claim 3, wherein the synthetic pyrethroid is lambda cyhalothrin.

7. The method as set forth in claim 3, wherein the synthetic pyrethroid is other than tefluthrin.

8. The method as set forth in claim 3, wherein the synthetic pyrethroid is one having a water solubility or a vapor pressure that is lower than that of tefluthrin.

9. The method as set forth in claim 3, where the synthetic pyrethroid is one having a water solubility of not over 10 mg/l at 20° C.

10. The method as set forth in claim 3, wherein the synthetic pyrethroid is one having a water solubility of not over 1 mg/l at 20° C.

11. The method as set forth in claim 3, wherein the synthetic pyrethroid is one having a water solubility of not over 0.018 mg/l at 20° C.

12. The method as set forth in claim 3, wherein the synthetic pyrethroid is one having a water solubility of not over 0.01 mg/l at 20° C.

13. The method as set forth in claim 3, wherein the synthetic pyrethroid is one having a vapor pressure of not over 50 mPa at 20° C.

14. The method as set forth in claim 3, wherein the synthetic pyrethroid is one having a vapor pressure of not over 6 mPa at 20° C.

15. The method as set forth in claim 3, wherein the synthetic pyrethroid is one having a vapor pressure of not over 1 mPa at 20° C.

16. The method as set forth in claim 10, wherein the synthetic pyrethroid is one having a vapor pressure of not over 6 mPa at 20° C.

17. The method as set forth in claim 3, wherein the synthetic pyrethroid is one having a water solubility that is less than 0.02 mg/l (20° C.) and/or a vapor pressure of less than 8 mPa at 20° C.

18. The method as set forth in claim 3, wherein the synthetic pyrethroid is one having a water solubility that is less than 0.015 mg/l (20° C.) and/or a vapor pressure of less than 6 mPa 20° C.

19. The method as set forth in claim 3, wherein the synthetic pyrethroid is selected on the basis of its activity in preventing damage to the shoots and foliage of the plant by an insect.

20. The method as set forth in claim 3, wherein the synthetic pyrethroid is selected on the basis of its activity in preventing damage to the shoots and foliage of the plant by a *Lepidopteran* sp. insect.

21. The method as set forth in claim 3, wherein the synthetic pyrethroid is selected on the basis of its activity in preventing damage to the shoots and foliage of the plant by a cutworm.

22. A seed having an exogenous gene that encodes for the production of a protein having activity against European corn borer or corn root worm and having adhered thereto at least one pyrethrin or synthetic pyrethroid that is selected on the basis of having activity against at least one pest other than European corn borer or corn root worm in an amount effective to provide protection to the shoots and foliage of the plant against damage by the pest.

23. The seed as set forth in claim 22, wherein the seed is selected from the group consisting of corn, soybean, cotton, rice, sorghum, sugar beet, wheat, barley, rye, sunflower, tomato, sugarcane, tobacco, rape and oats.

24. The seed as set forth in claim 22, wherein the seed is selected from the group consisting of corn, soybean and cotton seed.

25. The seed as set forth in claim 22, wherein the seed is corn seed.

26. The seed as set forth in claim 22, wherein the pyrethrin or synthetic pyrethroid is selected from the group consisting of (s)-cyano(3-phenoxyphenyl)methyl 4-chloro alpha (1-methylethyl)benzeneacetate (fenvalerate), (S)-cyano (3-phenoxyphenyl)methyl (S)-4-chloro-alpha-(1-methylethyl)benzeneacetate (esfenvalerate), (3-phenoxyphenyl)-methyl(+) cis-trans-3-(2,2-dichoroethenyl)-2,2-dimethylcyclopropanecarboxylate (permethrin), (±) alpha-cyano-(3-phenoxyphenyl)methyl(+)-cis,trans-3-(2,2- dichloroethenyl)-2,2-dimethyl-cyclopropane carboxylate (cypermethrin), beta-cypermethrin, theta cypermethrin, S-cyano (3-phenoxyphenyl)methyl (±) cis/trans 3-(2,2-dichloroethenyl) 2,2 dimethylcyclopropane carboxylate (zeta-cypermethrin), (s)-alpha-cyano-3-phenoxybenzyl (IR, 3R)-3-(2,2-dibromovinyl)-2,2-dimethyl cyclopropanecarboxylate (deltamethrin), alpha-cyano-3-phenoxybenzyl 2,2,3,3,-tetramethyl cyclopropoanecarboxylate (fenpropathrin), (RS)-alpha-cyano-3-phenoxybenzyl(R)-2-[2-chloro-4-(trifluoromethyl)anilino]-3-methylbutanoate (tau-fluvalinate), (2,3,5,6-tetrafluoro-4-methylphenyl)-methyl-(1 alpha,3 alpha)-(Z)-(±)-3-(2-chloro-3,3,3-trifluoro-1-propenyl)-2,2-dimethylcyclopropanecarboxylate (tefluthrin), (±)-cyano (3-phenoxyphenyl)methyl (±)-4-(difluoromethoxy)-alpha-(1-methyl ethyl) benzeneacetate (flucythrinate), cyano(4-fluoro-3-phenoxyphenyl)methyl 3-[2-chloro-2-(4-chlorophenyl)ethenyl]-2,2-dimethylcyclopropanecarboxylate (flumethrin), cyano(4-fluoro-3-phenoxyphenyl)methyl 3-(2,2-dichloroethenyl)-2,2-dimethyl-cyclopropanedarboxylate (cyfluthrin), beta cyfluthrin, transfluthrin, (S)-alpha-cyano-3-phenoxybenzyl(Z)-(IR-cis)-2,2-dimethyl-3-[2-(2,2,2-trifluoro-trifluoromethyl-ethoxycarbonyl)vinyl]cyclopropane carboxylate (acrinathrin), (IR cis) S and (IS cis) R enantiomer isomer pair of alpha-cyano-3-phenoxybenzyl-3-(2,2-dichlorovinyl)-2,2-dimethylcyclopropane carboxylate (alphacypermethrin), [IR,3S)3(1'RS)(1',2',2',2'-tetrabromoethyl)]-2,2-dimethyl cyclopropanecarboxylic acid (s)-alpha-cyano-3-phenoxybenzyl ester (tralomethrin), cyano-(3-phenoxyphenyl)methyl 2,2-dichloro-1-(4-ethoxyphenyl) cyclopropane carboxylate (cycloprothrin), [1α,3α(Z)]-(±)-cyano-(3-phenoxyphenyl)methyl 3-(2-chloro-3,3,3-trifluoro-1-propenyl)-2,2-cimethylcyclopropanecarboxylate (cyhalothrin), [1 alpha (s),3 alpha(z)]-cyano(3-phenoxyphenyl)methyl-3-(2-chloro-3,3,3-trifluoro-1-propenyl)-2,2-dimethylcyclopropane carboxylate (lambda cyhalothrin), (2-methyl [1,1'-biphenyl]-3-yl)methyl 3-(2-chloro-3,3,3-trifluoro-1-propenyl)-2,2-dimethyl-cyclopropanecarboxylate (bifenthrin), 5-1-benzyl-3-furylmethyl-d-cis(1R,3S, E)2,2-dimethyl-3-(2-oxo,-2,2,4,5 tetrahydro thiophenylidenemethyl)cyclopropane carboxylate (kadethrin, RU15525), [5-(phenyl methyl)-3-furanyl]-3-furanyl 2,2-dimethyl-3-(2-methyl-1-propenyl)cyclopropane carboxylate (resmethrin), (1R-trans)-[5-(phenylmethyl)-3-furanyl]methyl 2,2-dimethyl-3-(2-methyl-1-propenyl)cyclopropanecarboxylate (bioresmethrin), 3,4,5,6-tetrahydro-phthalimidomethyl-(IRS)-cis-trans-chrysanthemate (tetramethrin), 3-phenoxybenzyl-d,l-cis,trans 2,2-dimethyl-3-(2-methylpropenyl)cyclopropane carboxylate (phenothrin), empenthrin, cyphenothrin, prallethrin, imiprothrin, (RS)-3-allyl-2-methyl-4-oxcyclopent-2-enyl-(1A,3R;1R,3S)-2,2-dimethyl-3-(2-methylprop-1-enyl)cyclopropane carboxylate (allethrin), bioallethrin, ZXI8901, and mixtures thereof.

27. The seed as set forth in claim 22, wherein the pyrethrin or synthetic pyrethroid is tefluthrin.

28. The seed as set forth in claim 22, wherein the pyrethrin or synthetic pyrethroid is lambda cyhalothrin.

29. The seed as set forth in claim 22, wherein the synthetic pyrethroid is other than tefluthrin.

30. The seed as set forth in claim 22, wherein the synthetic pyrethroid is one having a water solubility or a vapor pressure that is lower than that of tefluthrin.

31. The seed as set forth in claim 22, where the synthetic pyrethroid is one having a water solubility of not over 10 mg/l at 20° C.

32. The seed as set forth in claim 22, wherein the synthetic pyrethroid is one having a water solubility of not over 1 mg/l at 20° C.

33. The seed as set forth in claim 22, wherein the synthetic pyrethroid is one having a water solubility of not over 0.018 mg/l at 20° C.

34. The seed as set forth in claim 22, wherein the synthetic pyrethroid is one having a water solubility of not over 0.01 mg/l at 20° C.

35. The seed as set forth in claim 22, wherein the synthetic pyrethroid is one having a vapor pressure of not over 50 mPa at 20° C.

36. The seed as set forth in claim 22, wherein the synthetic pyrethroid is one having a vapor pressure of not over 6 mPa at 20° C.

37. The seed as set forth in claim 22, wherein the synthetic pyrethroid is one having a vapor pressure of not over 1 mPa at 20° C.

38. The seed as set forth in claim 32, wherein the synthetic pyrethroid is one having a vapor pressure of not over 6 mPa at 20° C.

39. The seed as set forth in claim 22, wherein the synthetic pyrethroid is one having a water solubility that is less than 0.02 mg/l (20° C.) and/or a vapor pressure of less than 8 mPa at 20° C.

40. The seed as set forth in claim 22, wherein the synthetic pyrethroid is one having a water solubility that is less than 0.015 mg/l (20° C.) and/or a vapor pressure of less than 6 mPa at 20° C.

* * * * *